US007790954B2

(12) United States Patent
Davies et al.

(10) Patent No.: US 7,790,954 B2
(45) Date of Patent: Sep. 7, 2010

(54) GENERATION OF PLANTS WITH ALTERED OIL, PROTEIN, OR FIBER CONTENT

(75) Inventors: John P. Davies, Portland, OR (US); Hein Tsoeng (Medard) Ng, Charlottesville, VA (US)

(73) Assignee: Agrigenetics, Inc., Indianapolis, IN (US)

( * ) Notice: Subject to any disclaimer, the term of this patent is extended or adjusted under 35 U.S.C. 154(b) by 269 days.

(21) Appl. No.: 11/958,113

(22) Filed: Dec. 17, 2007

(65) Prior Publication Data

US 2008/0280010 A1 Nov. 13, 2008

Related U.S. Application Data

(60) Provisional application No. 60/870,345, filed on Dec. 15, 2006, provisional application No. 60/870,353, filed on Dec. 15, 2006, provisional application No. 60/870,355, filed on Dec. 15, 2006, provisional application No. 60/870,357, filed on Dec. 15, 2006.

(51) Int. Cl.
*A01H 5/00* (2006.01)
*C12N 15/82* (2006.01)

(52) U.S. Cl. ..................... 800/281; 800/298; 435/320.1

(58) Field of Classification Search ....................... None
See application file for complete search history.

(56) References Cited

U.S. PATENT DOCUMENTS

| | | | |
|---|---|---|---|
| 5,322,783 | A | 6/1994 | Tomes et al. |
| 5,538,880 | A | 7/1996 | Lundquist et al. |
| 5,550,318 | A | 8/1996 | Adams et al. |
| 5,563,055 | A | 10/1996 | Townsend et al. |
| 5,610,042 | A | 3/1997 | Chang et al. |
| 5,639,790 | A | 6/1997 | Voelker et al. |
| 5,704,160 | A | 1/1998 | Bergquist et al. |
| 5,952,544 | A | 9/1999 | Browse et al. |
| 6,229,033 | B1 | 5/2001 | Knowlton |
| 6,248,939 | B1 | 6/2001 | Leto et al. |
| 2003/0046723 | A1 | 3/2003 | Heard et al. |
| 2004/0019927 | A1 | 1/2004 | Sherman et al. |
| 2004/0025202 | A1 | 2/2004 | Laurie et al. |
| 2006/0150283 | A1 | 7/2006 | Alexandrov et al. |
| 2006/0277630 | A1 | 12/2006 | Lightner et al. |

FOREIGN PATENT DOCUMENTS

| | | |
|---|---|---|
| EP | 1033405 | 9/2000 |
| WO | 94/11516 | 5/1994 |
| WO | 95/06128 | 3/1995 |
| WO | 2004/093528 | 11/2004 |
| WO | 2004/093532 | 11/2004 |
| WO | 2005/047516 | 5/2005 |
| WO | 2005/107437 | 11/2005 |
| WO | 2007/053482 | 5/2007 |

OTHER PUBLICATIONS

Tabata et al., Database UniProt, Mar. 2001.*

Anoop et al., "Modulation of citrate metabolism alters aluminum tolerance in yeast and transgenic canola overexpressing a mitochondrial citrate synthase," *Plant Physiol.* 132, 2205-2217 (2003).

Bateman et al., "Pfam 3.1: 1313 multiple alignments and profile HMMs match the majority of proteins," *Nucleic Acids Res.*, 27:260-262 (1999).

Beisson, et al., "Arabidopsis genes involved in acyl lipid metabolism. A 2003 census of the candidates, a study of the distribution of expressed sequence tags in organs, and a web-based database," *Plant Physiol.*, 132:681-697 (2003).

Bert et al., "Comparative genetic analysis of quantitative traits in sunflower (*Helianthus annuus* L.). 2. Characterisation of QTL involved in developmental and agronomic traits," *Theor. Appl. Genet.*, 107:181-9, (2003).

Browse et al., "Fluxes through the prokaryotic and eukaryotic pathways of lipid synthesis in the '16:3' plant *Arabidopsis thaliana,*" *Biochem J.* 235:25-31 (1986).

Chapple and Carpita, "Plant cell walls as targets for biotechnology," *Current Opinion in Plant Biology*, 1:179-185 (1998).

Christensen et al., *9th International Conference on Arabidopsis Research,* Univ. of Wisconsin-Madison, Jun. 24-28, Abstract 165 (1998).

Christou et al., "Inheritance and expression of foreign genes in transgenic soybean plants," *Proc. Natl. Acad. Sci. USA*, 86:7500-7504 (1989).

Colbert et al., "High-throughput screening for induced point mutations," *Plant Physiol.* 126:480-484 (2001).

De Block et al., "Transformation of *Brassica napus* and *Brassica oleracea* Using *Agrobacterium tumefaciens* and the Expression of the bar and neo Genes in the Transgenic Plants," *Plant Physiol.*, 91:694-701 (1989).

Dehesh et al., "Overexpression of 3-ketoacyl-acyl-carrier protein synthase IIIs in plants reduces the rate of lipid synthesis," *Plant Physiol.*, 125:1103-1114 (2001).

Douglas et al., "Nutritional evaluation of low phytate and high protein corns," *Poultry Sci.* 79:1586-1591 (2000).

Eastmond et al., "Re-examining the role of the glyoxylate cycle in oilseeds," *Trends Plant Sci.*, 6:72-78 (2001).

Eccleston et al., "Expression of lauroyl-acyl carrier protein thioesterase in *Brassica napus* seeds induces pathways for both fatty acid oxidation and biosynthesis and implies a set point for triacylglycerol accumulation," *Plant Cell.* 10:613-622 (1998).

Edwards et al., "Protein and energy evaluation of soybean meals processed from genetically modified high-protein soybeans," *Poultry Sci.* 79:525-527 (1999).

(Continued)

*Primary Examiner*—Eileen B O Hara
(74) *Attorney, Agent, or Firm*—Donald R. Stuart; Klarquist Sparkman LLP

(57) ABSTRACT

The present invention is directed to plants that display an improved oil quantity phenotype or an improved meal quality phenotype due to altered expression of an HIO nucleic acid. The invention is further directed to methods of generating plants with an improved oil quantity phenotype or improved meal quality phenotype.

24 Claims, No Drawings

OTHER PUBLICATIONS

Everett et al., "Genetic engineering of sunflower (*Helianthus annuus* L.)," *Bio/Technology*, 5:1201 (1987).
Falco et al., "Transgenic canola and soybean seeds with increased lysine," *Bio/Technology*, 13:577-582 (1995).
Fatland et al., "Molecular biology of cytosolic acetyl-CoA generation," *Biochem Soc Trans.*, 28:593-595 (2000).
Fatland et al., "Reverse genetic characterization of cytosolic acetyl-CoA generation by ATP-citrate lyase in *Arabidopsis," Plant Cell.*, 17:182-203 (2004).
Feldmann et al., "A Dwarf Mutant of *Arabidopsis* Generated by T-DNA Insertion Mutagenesis," *Science*, 243:1351-1354 (1989).
Focks and Benning, "wrinkled1: A novel, low-seed-oil mutant of *Arabidopsis* with a deficiency in the seed-specific regulation of carbohydrate metabolism," *Plant Physiol*., 118:91-101 (1998).
Fridborg et al., "The *Arabidopsis* dwarf mutant *shi* exhibits reduced gibberellin responses conferred by overexpression of a new putative zinc finger protein," *Plant Cell*, 11:1019-1032 (1999).
Girke et al., "Microarray analysis of developing *Arabidopsis* seeds," *Plant Physiol*. 124:1570-1581 (2000).
Hayashi et al., "Activation of a plant gene by T-DNA tagging: auxin-independent growth in vitro," *Science*, 258:1350-1353 (1992).
Honig and Rackis, "Determination of the total pepsin-pancreatin indigestible content (dietary fiber) of soybean products, wheat bran, and corn bran," *J. Agri. Food Chem*., 27:1262-1266 (1979).
Jako et al., "Seed-specific over-expression of an *Arabidopsis* cDNA encoding a diacylglycerol acyltransferase enhances seed oil content and seed weight," *Plant Physiol.*, 126(2):861-74 (2001).
James and Dooner, "Isolation of EMS-induced mutants in *Arabidopsis* altered in seed fatty acid composition," *Theor. Appl. Genet*., 80:241-245 (1990).
Kardailsky et al., "Activation tagging of the floral inducer FT," *Science*, 286:1962-1965 (1999).
Katavic et al., "Alteration of seed fatty acid composition by an ethyl methanesulfonate-induced mutation in *Arabidopsis thaliana* affecting diacylglycerol acyltransferase activity," *Plant Physiol.*, 108:399-409 (1995).
Katavic et al., "Utility of the *Arabidopsis* FAE1 and yeast SLC1-1 genes for improvements in erucic acid and oil content in rapeseed," *Biochem Soc Trans*., 28:935-937 (2000).
Kline et al., "High velocity microprojectiles for delivering nucleic acids into living cells," *Nature*, 327:70-73 (1987).
Larson et al., "Acyl CoA profiles of transgenic plants that accumulate medium-chain fatty acids indicate inefficient storage lipid synthesis in developing oilseeds," *Plant J*., 32:519-527 (2002).
Lemieux et al., "Mutants of *Arabidopsis* with alterations in seed lipid fatty acid composition," *Theor. Appl. Genet*., 80:234-240 (1990).
Lin et al., "The Pex16p homolog SSE1 and storage organelle formation in *Arabidopsis* seeds," *Science*, 284:328-330 (1999).
Lionneton et al., "Development of an AFLP-based linkage map and localization of QTLs for seed fatty acid content in condiment mustard (*Brassica juncea*)," *Genome*, 45:1203-15 (2002).
Liu et al., "A transcriptional switch in the expression of yeast tricarboxylic acid cycle genes in response to a reduction or loss of respiratory function," *Mol Cell Biol.*, 19:6720-6728 (1999).
McCallum et al., "Targeted screening for induced mutations," *Nature Biotechnology*, 18:455-457 (2000).
Mekhedov et al., "Toward a functional catalog of the plant genome. A survey of genes for lipid biosynthesis," *Plant Physiol*., 122:389-402 (2000).
Moire et al., "Impact of unusual fatty acid synthesis on futile cycling through beta-oxidation and on gene expression in transgenic plants," *Plant Physiol*., 134:432-442 (2004).
Moore et al., "Chromatography of Amino Acids on Sulfonated Polystyrene Resins," *Anal. Chem*., 30:1185-1190 (1958).
Mulder et al., "The InterPro Database, 2003 brings increased coverage and new features," *Nucleic Acids Res*., 31:315-318, 2003.
Neuhaus et al., "Nonphotosynthetic Metabolism in Plastids," *Annu Rev Plant Physiol Plant Mol Biol.*, 51:111-140 (2000).
O'Hara et al., "Fatty acid and lipid biosynthetic genes are expressed at constant molar ratios but different absolute levels during embryogenesis," *Plant Physiol*., 129:310-320 (2002).
Okuley et al., "*Arabidopsis FAD2* gene encodes the enzyme that is essential for polyunsaturated lipid synthesis," *Plant Cell*, 6:147-158 (1994).
Parsons et al., "Nutritional evaluation of soybean meals varying in oligosaccharide content," *Poultry Sci.*, 79:1127-1131 (2000).
Pritchard et al., "Germination and storage reserve mobilization are regulated independently in *Arabidopsis," Plant J.*, 31:639-647 (2002).
Rangasamy et al., "Genetic enhancement of fatty acid synthesis by targeting rat liver ATP:citrate lyase into plastids of tobacco," *Plant Physiol*., 122:1231-1238 (2000).
Rangasamy et al., "Compartmentation of ATP:citrate lyase in plants," *Plant Physiol*. 122:1225-1230 (2000).
Ratledge et al., "Correlation of ATP/citrate lyase activity with lipid accumulation in developing seeds of *Brassica napus* L. Lipids," 32:7-12 (1997).
Rawsthorne, "Carbon flux and fatty acid synthesis in plants," *Prog Lipid Res*. 41:182-196 (2002).
Ruuska et al., "Contrapuntal networks of gene expression during *Arabidopsis* seed filling," *Plant Cell*., 14:1191-1206 (2002).
Rylott et al., "Co-ordinate regulation of genes involved in storage lipid mobilization in *Arabidopsis thaliana," Biochem Soc Trans*., 29:283-287 (2001).
Schaffer et al., "The late elongated hypocotyl mutation of *Arabidopsis* disrupts circadian rhythms and the photoperiodic control of flowering," *Cell*, 93:1219-1229 (1998).
Schnarrenberger et al., "Evolution of the enzymes of the citric acid cycle and the glyoxylate cycle of higher plants. A case study of endosymbiotic gene transfer," *Eur J Biochem*., 269:868-883 (2002).
Schnurr et al., "Characterization of an acyl-CoA synthetase from *Arabidopsis thaliana," Biochem Soc Trans.*, 28:957-958 (2000).
Shewry, "Seed storage proteins: structures and biosynthesis," *Plant Cell*, 7:945-956 (1995).
Shockey et al., "Characterization of the AMP-binding protein gene family in *Arabidopsis thaliana*: will the real acyl-CoA synthetases please stand up?" *Biochem Soc Trans.*, 28:955-957 (2000).
Thelen et al., "Biotin carboxyl carrier protein isoforms in Brassicaceae oilseeds," *Biochem Soc Trans*., 28:595-598 (2000).
Weigel et al., "Activation tagging in *Arabidopsis," Plant Physiology*, 122:1003-1013 (2000).
White et al., "A new set of *Arabidopsis* expressed sequence tags from developing seeds. The metabolic pathway from carbohydrates to seed oil," *Plant Physiol*., 124:1582-1594 (2000).
Wilson et al., "A Dissociation insertion causes a semidominant mutation that increases expression of Tiny, an *Arabidopsis* gene related to APETALA2," *Plant Cell*, 8:659-671 (1996).
Yadav et al., "Cloning of higher plant omega-3 fatty acid desaturases," *Plant Physiol*., 103:467-476 (1993).

* cited by examiner

GENERATION OF PLANTS WITH ALTERED OIL, PROTEIN, OR FIBER CONTENT

CROSS REFERENCE TO RELATED APPLICATION(S)

This application claims the benefit of U.S. Provisional Application Nos. 60/870,345, 60/870,353, 60/870,355, and 60/870,357, all of which were filed Dec. 15, 2006, and all of which are incorporated herein by reference.

FIELD OF THE DISCLOSURE

The present disclosure is related to modified plants with altered oil, protein, and/or fiber content, as well as methods of making modified plants having altered oil, protein, and/or fiber content and producing oil from such plants.

BACKGROUND

The ability to manipulate the composition of crop seeds, particularly the content and composition of seed oil and protein, as well as the available metabolizable energy ("AME") in the seed meal in livestock, has important applications in the agricultural industries, relating both to processed food oils and to animal feeds. Seeds of agricultural crops contain a variety of valuable constituents, including oil, protein and starch. Industrial processing can separate some or all of these constituents for individual sale in specific applications. For instance, nearly 60% of the U.S. soybean crop is crushed by the soy processing industry. Soy processing yields purified oil, which is sold at high value, while the remaining seed meal is sold for livestock feed (U.S. Soybean Board, 2001 Soy Stats). Canola seed is also crushed to produce oil and the co-product canola meal (Canola Council of Canada). Canola meal contains a high percentage of protein and a good balance of amino acids but because it has a high fiber and phytate content, it is not readily digested by livestock (Slominski, B. A., et al., 1999 Proceedings of the 10$^{th}$ International Rapeseed Congress, Canberra, Australia) and has a lower value than soybean meal.

Over 55% of the corn produced in the U.S. is used as animal feed (Iowa Corn Growers Association). The value of the corn is directly related to its ability to be digested by livestock. Thus, it is desirable to maximize both oil content of seeds and the AME of meal. For processed oilseeds such as soy and canola, increasing the absolute oil content of the seed will increase the value of such grains, while increasing the AME of meal will increase its value. For processed corn, either an increase or a decrease in oil content may be desired, depending on how the other major constituents are to be used. Decreasing oil may improve the quality of isolated starch by reducing undesired flavors associated with oil oxidation. Alternatively, when the starch is used for ethanol production, where flavor is unimportant, increasing oil content may increase overall value.

In many feed grains, such as corn and wheat, it is desirable to increase seed oil content, because oil has higher energy content than other seed constituents such as carbohydrate. Oilseed processing, like most grain processing businesses, is a capital-intensive business; thus small shifts in the distribution of products from the low valued components to the high value oil component can have substantial economic impacts for grain processors. In addition, increasing the AME of meal by adjusting seed protein and fiber content and composition, without decreasing seed oil content, can increase the value of animal feed.

Biotechnological manipulation of oils has been shown to provide compositional alteration and improvement of oil yield. Compositional alterations include high oleic acid soybean and corn oil (U.S. Pat. Nos. 6,229,033 and 6,248,939), and laurate-containing seeds (U.S. Pat. No. 5,639,790), among others. Work in compositional alteration has predominantly focused on processed oilseeds, but has been readily extendable to non-oilseed crops, including corn. While there is considerable interest in increasing oil content, the only currently practiced biotechnology in this area is High-Oil Corn (HOC) technology (DuPont, U.S. Pat. No. 5,704,160). HOC employs high oil pollinators developed by classical selection breeding along with elite (male-sterile) hybrid females in a production system referred to as TopCross. The TopCross High Oil system raises harvested grain oil content in maize from about 3.5% to about 7%, improving the energy content of the grain.

While it has been fruitful, the HOC production system has inherent limitations. First, the system of having a low percentage of pollinators responsible for an entire field's seed set contains inherent risks, particularly in drought years. Second, oil content in current HOC fields has not been able to achieve seed oil content above 9%. Finally, high-oil corn is not primarily a biochemical change, but rather an anatomical mutant (increased embryo size) that has the indirect result of increasing oil content. For these reasons, an alternative high oil strategy, particularly one that derives from an altered biochemical output, would be especially valuable.

Manipulation of seed composition has identified several components that improve the nutritive quality, digestibility, and AME in seed meal. Increasing the lysine content in canola and soybean (Falco et al., 1995 *Bio/Technology* 13:577-582) increases the availability of this essential amino acid and decreases the need for nutritional supplements. Soybean varieties with increased seed protein were shown to contain considerably more metabolizable energy than conventional varieties (Edwards et al., 1999, *Poultry Sci.* 79:525-527). Decreasing the phytate content of corn seed has been shown to increase the bioavailability of amino acids in animal feeds (Douglas et al., 2000, *Poultry Sci.* 79:1586-1591) and decreasing oligosaccharide content in soybean meal increases the metabolizable energy in the meal (Parsons et al., 2000, *Poultry Sci.* 79:1127-1131).

Soybean and canola are the most obvious target crops for the processed oil and seed meal markets since both crops are crushed for oil and the remaining meal sold for animal feed. A large body of commercial work (e.g., U.S. Pat. No. 5,952,544; PCT Application No. WO9411516) demonstrates that *Arabidopsis* is an excellent model for oil metabolism in these crops. Biochemical screens of seed oil composition have identified *Arabidopsis* genes for many critical biosynthetic enzymes and have led to identification of agronomically important gene orthologs. For instance, screens using chemically mutagenized populations have identified lipid mutants whose seeds display altered fatty acid composition (Lemieux et al., 1990, *Theor. Appl Genet.* 80: 234-240; James and Dooner, 1990, *Theor. Appl Genet.* 80: 241-245). T-DNA mutagenesis screens (Feldmann et al., 1989, *Science* 243: 1351-1354) that detected altered fatty acid composition identified the omega 3 desaturase (FAD3) and delta-12 desaturase (FAD2) genes (U.S. Pat. No. 5,952,544; Yadav et al., 1993, *Plant Physiol* 103: 467-476; Okuley et al., 1994, *Plant Cell* 6(1):147-158). A screen which focused on oil content rather than oil quality, analyzed chemically-induced mutants for wrinkled seeds or altered seed density, from which altered seed oil content was inferred (Focks and Benning, 1998, *Plant Physiol.* 118:91-101).

Another screen, designed to identify enzymes involved in production of very long chain fatty acids, identified a mutation in the gene encoding a diacylglycerol acyltransferase (DGAT) as being responsible for reduced triacyl glycerol accumulation in seeds (Katavic V et al., 1995, *Plant Physiol* 108(1):399-409). It was further shown that seed-specific over-expression of the DGAT cDNA was associated with increased seed oil content (Jako et al., 2001, *Plant Physiol* 126(2):861-74). *Arabidopsis* is also a model for understanding the accumulation of seed components that affect meal quality. For example, *Arabidopsis* contains albumin and globulin seed storage proteins found in many dicotyledonous plants including canola and soybean (Shewry 1995, *Plant Cell* 7:945-956). The biochemical pathways for synthesizing components of fiber, such as cellulose and lignin, are conserved within the vascular plants, and mutants of *Arabidopsis* affecting these components have been isolated (reviewed in Chapel and Carpita 1998, *Current Opinion in Plant Biology* 1:179-185).

Activation tagging in plants refers to a method of generating random mutations by insertion of a heterologous nucleic acid construct comprising regulatory sequences (e.g., an enhancer) into a plant genome. The regulatory sequences can act to enhance transcription of one or more native plant genes; accordingly, activation tagging is a fruitful method for generating gain-of-function, generally dominant mutants (see, e.g., Hayashi et al., 1992, *Science* 258: 1350-1353; Weigel D et al., 2000, *Plant Physiology*, 122:1003-1013). The inserted construct provides a molecular tag for rapid identification of the native plant whose mis-expression causes the mutant phenotype. Activation tagging may also cause loss-of-function phenotypes. The insertion may result in disruption of a native plant gene, in which case the phenotype is generally recessive.

Activation tagging has been used in various species, including tobacco and *Arabidopsis*, to identify many different kinds of mutant phenotypes and the genes associated with these phenotypes (Wilson et al., 1996, *Plant Cell* 8: 659-671; Schaffer et al., 1998, *Cell* 93: 1219-1229; Fridborg et al., 1999, *Plant Cell* 11: 1019-1032; Kardailsky et al., 1999, *Science* 286: 1962-1965; and Christensen S et al, 1998, $9^{th}$ *International Conference on Arabidopsis Research*, Univ. of Wisconsin-Madison, June 24-28, Abstract 165).

SUMMARY

Provided herein are modified plants having an altered phenotype. Modified plants with an altered phenotype may include an improved oil quantity and/or an improved meal quality phenotype. The altered phenotype in a modified plant may also include altered oil, protein, and/or fiber content in any part of the modified plant, for example in the seeds. In some embodiments of a modified plant, the altered phenotype is an increase in the oil content of the seed (a high oil phenotype). In other embodiments, the altered phenotype may be an increase in protein content in the seed and/or a decrease in the fiber content of the seed. Also provided is seed meal derived from the seeds of modified plants, wherein the seeds have altered protein content and/or altered fiber content. Further provided is oil derived from the seeds of modified plants, wherein the seeds have altered oil content. Any of these changes can lead to an increase in the AME from the seed or seed meal from modified plants, relative to control or wild-type plants. Also provided herein is meal, feed, or food produced from any part of the modified plant with an altered phenotype.

In certain embodiments, the disclosed modified plants include transgenic plants having a transformation vector comprising a HIO nucleotide sequence (or HIO gene alias) that encodes or is complementary to a sequence that encodes a "HIO" polypeptide. In particular embodiments, expression of a HIO polypeptide in a transgenic plant causes an altered oil content, an altered protein content, and/or an altered fiber content in the transgenic plant. In preferred embodiments, the transgenic plant is selected from the group consisting of plants of the *Brassica* species, including canola and rapeseed, soy, corn, sunflower, cotton, cocoa, safflower, oil palm, coconut palm, flax, castor, peanut, wheat, oat and rice. Also provided is a method of producing oil or seed meal, comprising growing the transgenic plant and recovering oil and/or seed meal from said plant. The disclosure further provides feed, meal, grain, or seed comprising a nucleic acid sequence that encodes a HIO polypeptide. The disclosure also provides feed, meal, grain, or seed comprising the HIO polypeptide, or an ortholog or paralog thereof.

Examples of the disclosed transgenic plant are produced by a method that comprises introducing into progenitor cells of the plant a plant transformation vector comprising a HIO nucleotide sequence that encodes, or is complementary to a sequence that encodes, a HIO polypeptide, and growing the transformed progenitor cells to produce a transgenic plant, wherein the HIO polynucleotide sequence is expressed, causing an altered phenotype in the transgenic plant. In some specific, non-limiting examples, the method produces transgenic plants wherein expression of the HIO polypeptide causes a high (increased) oil, high (increased) protein, and/or low (decreased) fiber phenotype in the transgenic plant, relative to control, non-transgenic, or wild-type plants.

Additional methods are disclosed herein of generating a plant having an altered phenotype, wherein a plant is identified that has a mutation or an allele in its HIO nucleic acid sequence that results in an altered phenotype, compared to plants lacking the mutation or allele. The mutated plant can be generated using one or more mutagens, for example a chemical mutagen, radiation, or ultraviolet light. In some embodiments of the method, the plant is bred to generate progeny which inherit the allele and express the altered phenotype. In particular embodiments of the method, the method employs candidate gene/QTL methodology or TILLING methodology.

Also provided herein is a modified plant cell having an altered phenotype. In some embodiments, the modified plant cell includes a transformation vector comprising a HIO nucleotide sequence that encodes or is complementary to a sequence that encodes a HIO polypeptide. In preferred embodiments, the transgenic plant cell is selected from the group consisting of plants of the *Brassica* species, including canola and rapeseed, soy, corn, sunflower, cotton, cocoa, safflower, oil palm, coconut palm, flax, castor, peanut, wheat, oat and rice. In other embodiments, the plant cell is a seed, pollen, propagule, or embryo cell. The disclosure also provides plant cells from a plant that is the direct progeny or the indirect progeny of a plant grown from said progenitor cells.

DETAILED DESCRIPTION

Terms

Unless otherwise indicated, all technical and scientific terms used herein have the same meaning as they would to one skilled in the art of the present disclosure. Practitioners are particularly directed to Sambrook et al. (*Molecular Cloning: A Laboratory Manual* (Second Edition), Cold Spring Harbor Press, Plainview, N.Y., 1989) and Ausubel F M et al. (*Current Protocols in Molecular Biology*, John Wiley & Sons, New York, N.Y., 1993) for definitions and terms of the art. It is to be understood that this disclosure is not limited to the particular methodology, protocols, and reagents described, as these may vary.

As used herein, the term "altered phenotype" refers to plants, or any part of a plant (for example, seeds, or meal produced from seeds), with an altered oil, protein, and/or fiber content (phenotype). As provided herein, altered oil, protein (for example, digestible protein) and/or fiber content includes either an increased or decreased level of oil, protein (for example, digestible protein) and/or fiber content in plants, seeds or seed meal. Any combination of these changes can lead to an altered phenotype. For example, in one specific non-limiting example, an altered phenotype can refer to increased oil and decreased fiber content. In another specific non-limiting example, an altered phenotype can refer to unchanged protein and decreased fiber content. In another specific non-limiting example, an altered phenotype can refer to increased oil and protein and decreased fiber. In yet other non-limiting examples, an altered phenotype can refer to increased oil and protein and unchanged fiber content; unchanged oil, increased protein, and decreased fiber content; or increased oil, increased protein, and decreased fiber content. It is also provided that any combination of these changes can lead to an increase in the AME (available metabolizable energy) from the seed or meal generated from the seed. An altered phenotype also includes an improved seed quality (ISQ) phenotype or an improved seed meal quality phenotype.

As used herein, the term "available metabolizable energy" (AME) refers to the amount of energy in the feed that is able to be extracted by digestion in an animal and is correlated with the amount of digestible protein and oil available in animal meal. AME is determined by estimating the amount of energy in the feed prior to feeding and measuring the amount of energy in the excreta of the animal following consumption of the feed. In one specific, non-limiting example, a modified plant with an increase in AME includes modified plants with altered seed oil, digestible protein, total protein and/or fiber content, resulting in an increase in the value of animal feed derived from the seed.

As used herein, the term "content" refers to the type and relative amount of, for instance, a seed or seed meal component.

As used herein, the term "seed oil" refers to the total amount of oil within the seed.

As used herein, the term "seed fiber" refers to non-digestible components of the plant seed including cellular components such as cellulose, hemicellulose, pectin, lignin, and phenolics.

As used herein, the term "meal" refers to seed components remaining following the extraction of oil from the seed. Examples of components of meal include protein and fiber.

As used herein, the term "seed total protein" refers to the total amount of protein within the seed.

As used herein, the term "seed digestible protein" refers to the seed protein that is able to be digested by enzymes in the digestive track of an animal. It is a subset of the total protein content.

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

A "heterologous" nucleic acid construct or sequence has a portion of the sequence that is not native to the plant cell in which it is expressed. Heterologous, with respect to a control sequence refers to a control sequence (i.e. promoter or enhancer) that does not function in nature to regulate the same gene the expression of which it is currently regulating. Generally, heterologous nucleic acid sequences are not endogenous to the cell or part of the genome in which they are present, and have been added to the cell by infection, transfection, microinjection, electroporation, or the like. A "heterologous" nucleic acid construct may contain a control sequence/DNA coding sequence combination that is the same as, or different from, a control sequence/DNA coding sequence combination found in the native plant. Specific, non-limiting examples of a heterologous nucleic acid sequence include a HIO nucleic acid sequence, or a fragment, derivative (variant), or ortholog or paralog thereof.

As used herein, the term "gene" means the segment of DNA involved in producing a polypeptide chain, which may or may not include regions preceding and following the coding region, e.g. 5' untranslated (5' UTR) or "leader" sequences and 3' UTR or "trailer" sequences, as well as intervening sequences (introns) between individual coding segments (exons) and non-transcribed regulatory sequences.

The term "homolog" refers to any gene that is related to a reference gene by descent from a common ancestral DNA sequence. The term "ortholog" refers to homologs in different species that evolved from a common ancestral gene by speciation. Typically, orthologs retain the same or similar function despite differences in their primary structure (mutations). The term "paralog" refers to homologs in the same species that evolved by genetic duplication of a common ancestral gene. In many cases, paralogs exhibit related (but not always identical functions). As used herein, the term homolog encompasses both orthologs and paralogs. To the extent that a particular species has evolved multiple related genes from an ancestral DNA sequence shared with another species, the term ortholog can encompass the term paralog.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed, or not expressed at all as a result of deliberate human intervention.

As used herein, the term "gene expression" refers to the process by which a polypeptide is produced based on the nucleic acid sequence of a gene. The process includes both transcription and translation; accordingly, "expression" may refer to either a polynucleotide or polypeptide sequence, or both. Sometimes, expression of a polynucleotide sequence will not lead to protein translation. "Over-expression" refers to increased expression of a polynucleotide and/or polypeptide sequence relative to its expression in a wild-type (or other reference [e.g., non-transgenic]) plant and may relate to a naturally-occurring or non-naturally occurring sequence. "Ectopic expression" refers to expression at a time, place, and/or increased level that does not naturally occur in the non-modified or wild-type plant. "Under-expression" refers to decreased expression of a polynucleotide and/or polypeptide sequence, generally of an endogenous gene, relative to its expression in a wild-type plant. The terms "mis-expression"

and "altered expression" encompass over-expression, under-expression, and ectopic expression.

The term "introduced" in the context of inserting a nucleic acid sequence into a cell, includes "transfection," "transformation," and "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

As used herein, a "plant cell" refers to any cell derived from a plant, including cells from undifferentiated tissue (e.g., callus), as well as from plant seeds, pollen, propagules, and embryos.

As used herein, the terms "native" and "wild-type" relative to a given plant trait or phenotype refers to the form in which that trait or phenotype is found in the same variety of plant in nature. In one embodiment, a wild-type or native plant is also a control plant. In another embodiment, a wild-type or native plant is a non-transgenic or non-mutated plant. In yet another embodiment, a wild-type or native plant is a non-modified plant.

As used herein, the term "modified" regarding a plant, refers to a plant with an altered phenotype (for example, a plant generated by genetic engineering, mutagenesis, or breeding methods). A genetically engineered plant can also be a transgenic plant. In particular embodiments, modified plants generated by breeding methods are first mutagenized using any one of a variety of mutagens, such as a chemical mutagen, radiation, or ultraviolet light. Modified plants can have any combination of an altered oil content, an altered protein content, and/or an altered fiber content in any part of the transgenic plant, for example the seeds, relative to a similar non-modified plant.

As used herein, the term "altered" refers to a change (either an increase or a decrease) of a plant trait or phenotype (for example, oil content, protein content, and/or fiber content) in a modified plant, relative to a similar non-modified plant. In one specific, non-limiting example, a modified plant with an altered trait includes a plant with an increased oil content, increased protein content, and/or decreased fiber content relative to a similar non-modified plant. In another specific, non-limiting example, a modified plant with an altered trait includes unchanged oil content, increased protein content, and/or decreased fiber content relative to a similar non-modified plant. In yet another specific, non-limiting example, a modified plant with an altered trait includes an increased oil content, increased protein content, and/or unchanged fiber content relative to a similar non-modified plant.

An "interesting phenotype (trait)" with reference to a modified plant refers to an observable or measurable phenotype demonstrated by a T1 and/or subsequent generation plant, which is not displayed by the corresponding non-modified plant (i.e., a genotypically similar plant that has been raised or assayed under similar conditions). An interesting phenotype may represent an improvement in the plant (for example, increased oil content, increased protein content, and/or decreased fiber content in seeds of the plant) or may provide a means to produce improvements in other plants. An "improvement" is a feature that may enhance the utility of a plant species or variety by providing the plant with a unique and/or novel phenotype or quality. Such modified plants may have an improved phenotype, such as an altered oil, protein, and/or fiber phenotype. Meal generated from seeds of a modified plant with an improved phenotype can have improved (increased) meal quality. In a specific, non-limiting example of meal with an improved (increased) quality phenotype, meal is generated from a seed of a modified plant, wherein the seed has increased protein content and/or decreased fiber content, relative to a similar non-modified plant.

The phrase "altered oil content phenotype" refers to a measurable phenotype of a modified plant, where the plant displays a statistically significant increase or decrease in overall oil content (i.e., the percentage of seed mass that is oil), as compared to the similar, but non-modified (for example, a non-transgenic or a non-mutated) plant. A high oil phenotype refers to an increase in overall oil content. An increase in oil content includes, in various embodiments, about a 1.0%, 1.5%, 2.0%, 2.5%, 3.0%, 3.5%, 4.0%, 4.5%, 5.0%, 7.5%, 10%, or more increase in oil content. Likewise, a decrease in oil content includes about a 1.0%, 1.5%, 2.0%, 2.5%, 3.0%, 3.5%, 4.0%, 4.5%, 5.0%, 7.5%, 10%, or more decrease in oil content, in various embodiments.

The phrase "altered protein content phenotype" refers to measurable phenotype of a modified plant, where the plant displays a statistically significant increase or decrease in overall protein content (i.e., the percentage of seed mass that is protein), as compared to the similar, but non-modified (for example, non-transgenic or non-mutated) plant. A high protein phenotype refers to an increase in overall protein content. An increase in protein content includes, in various embodiments, about a 1.0%, 1.5%, 2.0%, 2.5%, 3.0%, 3.5%, 4.0%, 4.5%, 5.0%, 7.5%, 10%, or more increase in total protein content. Likewise, an increase in digestible protein content includes, in various embodiments, about a 1.0%, 1.5%, 2.0%, 2.5%, 3.0%, 3.5%, 4.0%, 4.5%, 5.0%, 7.5%, 10%, or more increase in digestible protein content. A decrease in protein content includes about a 1.0%, 1.5%, 2.0%, 2.5%, 3.0%, 3.5%, 4.0%, 4.5%, 5.0%, 7.5%, 10%, or more decrease in total protein content, in various embodiments. Likewise, a decrease in digestible protein content includes, in various embodiments, about a 1.0%, 1.5%, 2.0%, 2.5%, 3.0%, 3.5%, 4.0%, 4.5%, 5.0%, 7.5%, 10%, or more decrease in digestible protein content. The phrase "altered fiber content phenotype" refers to measurable phenotype of a modified plant, where the plant displays a statistically significant increase or decrease in overall fiber content (i.e., the percentage of seed mass that is fiber), as compared to the similar, but non-modified (for example, non-transgenic or non-mutated) plant. A low fiber phenotype refers to decrease in overall fiber content. An increase in fiber content includes about a 1.0%, 1.5%, 2.0%, 2.5%, 3.0%, 3.5%, 4.0%, 4.5%, 5.0%, 7.5%, 10%, or more increase in fiber content. Likewise, a decrease in fiber content includes about a 1.0%, 1.5%, 2.0%, 2.5%, 3.0%, 3.5%, 4.0%, 4.5%, 5.0%, 7.5%, 10%, or more decrease in fiber content.

As used herein, a "mutant" or "mutated" polynucleotide sequence or gene differs from the corresponding wild-type polynucleotide sequence or gene either in terms of sequence or expression, where the difference contributes to an altered plant phenotype or trait. Relative to a plant or plant line, the term "mutant" or "mutated" refers to a plant or plant line which has an altered plant phenotype or trait, where the altered phenotype or trait is associated with the altered expression of a wild-type polynucleotide sequence or gene. The mutated polynucleotide sequence or gene can be generated by genetic engineering methods (such as activation tagging or transformation), by using one or more mutagens (for example, chemical mutagens, radiation, or ultraviolet light), or by using methods to alter a DNA sequence (for example, error prone PCR, DNA shuffling molecular breeding, site-directed mutagenesis, or introducing the gene into a mutagenizing organism such as *E. coli* or yeast strains that are deficient in DNA repair activity).

As used herein, the term "T1" refers to the generation of plants from the seed of T0 plants. The T1 generation is the first set of modified plants that can be selected by application of a selection agent, e.g., an antibiotic or herbicide, for which the modified plant contains the corresponding resistance gene. The term "T2" refers to the generation of plants by self-fertilization of the flowers of T1 plants, previously selected as being modified. T3 plants are generated from T2 plants, etc. As used herein, the "direct progeny" of a given plant derives from the seed (or, sometimes, other tissue) of that plant and is in the immediately subsequent generation; for instance, for a given lineage, a T2 plant is the direct progeny of a T1 plant. The "indirect progeny" of a given plant derives from the seed (or other tissue) of the direct progeny of that plant, or from the seed (or other tissue) of subsequent generations in that lineage; for instance, a T3 plant is the indirect progeny of a T1 plant.

As used herein, the term "plant part" includes any plant organ or tissue, including, without limitation, seeds, embryos, meristematic regions, callus tissue, leaves, roots, shoots, gametophytes, sporophytes, pollen, and microspores. Plant cells can be obtained from any plant organ or tissue and cultures prepared therefrom. Provided herein is a modified plant cell having an altered phenotype. In particular embodiments, the modified plant cell is a transgenic plant cell. The transgenic plant cell includes a transformation vector comprising an HIO nucleotide sequence that encodes or is complementary to a sequence that encodes an HIO polypeptide. In preferred embodiments, the transgenic plant cell is selected from the group consisting of plants of the *Brassica* species, including canola and rapeseed, soy, corn, sunflower, cotton, cocoa, safflower, oil palm, coconut palm, flax, castor, peanut, wheat, oat and rice. In other embodiments, the plant cell is a seed, pollen, propagule, or embryo cell. The disclosure also provides plant cells from a plant that is the direct progeny or the indirect progeny of a plant grown from said progenitor cells. The class of plants which can be used in the methods of the present invention is generally as broad as the class of higher plants amenable to transformation techniques, including both monocotyledonous and dicotyledonous plants.

As used herein, "transgenic plant" includes a plant that comprises within its genome a heterologous polynucleotide. The heterologous polynucleotide can be either stably integrated into the genome, or can be extra-chromosomal. Preferably, the polynucleotide of the present invention is stably integrated into the genome such that the polynucleotide is passed on to successive generations. A plant cell, tissue, organ, or plant into which the heterologous polynucleotides have been introduced is considered "transformed," "transfected," or "transgenic." Direct and indirect progeny of transformed plants or plant cells that also contain the heterologous polynucleotide are also considered transgenic.

Disclosed herein are modified plants having an altered phenotype. Modified plants with an altered phenotype may include an improved (increased) oil quantity and/or an improved (increased) meal quality, as compared to the similar, but non-modified (for example, non-transgenic or non-mutated) plant. Modified plants with an altered phenotype may include altered oil, protein, and/or fiber content in any part of the modified plant, for example in the seeds, as compared to the similar, but non-modified (for example, non-transgenic or non-mutated) plant. In some embodiments of a modified plant, for example in plants with an improved or increased oil content phenotype, the altered phenotype includes an increase in the oil content of the seed (a high oil phenotype) from the plant, as compared to the similar, but non-modified (non-transgenic or non-mutated) plant. An increase in oil content includes, in various embodiments, about a 1.0%, 1.5%, 2.0%, 2.5%, 3.0%, 3.5%, 4.0%, 4.5%, 5.0%, 7.5%, 10%, or more increase in oil content. The altered phenotype can be an increase in one or more fatty acids, such as oleic acid, with a concomitant decrease in other fatty acids such as linoleic or linolinic acids. A change in fatty acid content includes about a 5%, 10%, 20%, 30%, 40%, 50%, 60%, 70%, 80%, 90%, 100% or more increase in a specific fatty acid. In other embodiments of a modified plant, for example in plants with an improved or increased meal quality phenotype, the altered phenotype may be an increase in protein content in the seed and/or a decrease in the fiber content of the seed. An increase in protein content includes about a 1.0%, 1.5%, 2.0%, 2.5%, 3.0%, 3.5%, 4.0%, 4.5%, 5.0%, 7.5%, 10%, or more increase in protein content, for instance total protein content or digestible protein content. This change in seed protein content can be the result of altered amounts of seed storage proteins such as albumins, globulins prolamins, and glutelins. A decrease in fiber content includes about a 1.0%, 1.5%, 2.0%, 2.5%, 3.0%, 3.5%, 4.0%, 4.5%, 5.0%, 7.5%, 10%, or more decrease in fiber content. This change in fiber content can be the result of altered amounts of fibrous components such as cellulose, hemicellulose, lignin and pectins.

Also provided is seed meal derived from the seeds of modified plants, wherein the seeds have altered (for example, increased) protein (for example, digestible) content and/or altered (for example, decreased) fiber content. Further provided is oil derived from the seeds of modified plants, wherein the seeds have altered oil content. Any of these changes can lead to an increase in the AME from the seed or seed meal from modified plants, relative to control, non-transgenic, or wild-type plants. An increase in the AME includes about a 1.0%, 1.5%, 2.0%, 2.5%, 3.0%, 3.5%, 4.0%, 4.5%, 5.0%, 7.5%, 10%, or more increase in AME in the seed or seed meal, in various embodiments. Also provided herein is meal, feed, or food produced from any part of the modified plant with an altered phenotype.

In certain embodiments, the disclosed transgenic plants comprise a transformation vector comprising a HIO nucleotide sequence that encodes or is complementary to a sequence that encodes a "HIO" polypeptide. In particular embodiments, expression of a HIO polypeptide in a transgenic plant causes an altered oil content, an altered protein content, and/or an altered fiber content in the transgenic plant. In preferred embodiments, the transgenic plant is selected from the group consisting of plants of the *Brassica* species, including canola and rapeseed, soy, corn, sunflower, cotton, cocoa, safflower, oil palm, coconut palm, flax, castor, peanut, wheat, oat and rice. Also provided is a method of producing oil or seed meal, comprising growing the transgenic plant and recovering oil and/or seed meal from said plant. The disclosure further provides feed, meal, grain, or seed comprising a nucleic acid sequence that encodes a HIO polypeptide. The disclosure also provides feed, meal, grain, or seed comprising the HIO polypeptide, or an ortholog or paralog thereof.

Various methods for the introduction of a desired polynucleotide sequence encoding the desired protein into plant cells are available and known to those of skill in the art and include, but are not limited to: (1) physical methods such as microinjection, electroporation, and microprojectile mediated delivery (biolistics or gene gun technology); (2) virus mediated delivery methods; and (3) *Agrobacterium*-mediated transformation methods.

The most commonly used methods for transformation of plant cells are the *Agrobacterium*-mediated DNA transfer process and the biolistics or microprojectile bombardment mediated process (i.e., the gene gun). Typically, nuclear transformation is desired but where it is desirable to specifically transform plastids, such as chloroplasts or amyloplasts, plant plastids may be transformed utilizing a microprojectile-mediated delivery of the desired polynucleotide.

*Agrobacterium*-mediated transformation is achieved through the use of a genetically engineered soil bacterium belonging to the genus *Agrobacterium*. A number of wild-type and disarmed strains of *Agrobacterium tumefaciens* and *Agrobacterium rhizogenes* harboring Ti or Ri plasmids can be used for gene transfer into plants. Gene transfer is done via the transfer of a specific DNA known as "T-DNA" that can be genetically engineered to carry any desired piece of DNA into many plant species.

*Agrobacterium*-mediated genetic transformation of plants involves several steps. The first step, in which the virulent *Agrobacterium* and plant cells are first brought into contact with each other, is generally called "inoculation." Following the inoculation, the *Agrobacterium* and plant cells/tissues are permitted to be grown together for a period of several hours to several days or more under conditions suitable for growth and T-DNA transfer. This step is termed "co-culture." Following co-culture and T-DNA delivery, the plant cells are treated with bactericidal or bacteriostatic agents to kill or limit the growth of the *Agrobacterium* remaining in contact with the explant and/or in the vessel containing the explant. If this is done in the absence of any selective agents to promote preferential growth of transgenic versus non-transgenic plant cells, then this is typically referred to as the "delay" step. If done in the presence of selective pressure favoring transgenic plant cells, then it is referred to as a "selection" step. When a "delay" is used, it is typically followed by one or more "selection" steps.

With respect to microprojectile bombardment (U.S. Pat. No. 5,550,318; U.S. Pat. No. 5,538,880, U.S. Pat. No. 5,610,042; and PCT Publication WO 95/06128; each of which is specifically incorporated herein by reference in its entirety), particles are coated with nucleic acids and delivered into cells by a propelling force. Exemplary particles include those comprised of tungsten, platinum, and preferably, gold.

An illustrative embodiment of a method for delivering DNA into plant cells by acceleration is the Biolistics Particle Delivery System (BioRad, Hercules, Calif.), which can be used to propel particles coated with DNA or cells through a screen, such as a stainless steel or Nytex screen, onto a filter surface covered with monocot plant cells cultured in suspension.

Microprojectile bombardment techniques are widely applicable, and may be used to transform virtually any plant species. Examples of species that have been transformed by microprojectile bombardment include monocot species such as maize (PCT Publication No. WO 95/06128), barley, wheat (U.S. Pat. No. 5,563,055, incorporated herein by reference in its entirety), rice, oat, rye, sugarcane, and sorghum, as well as a number of dicots including tobacco, soybean (U.S. Pat. No. 5,322,783, incorporated herein by reference in its entirety), sunflower, peanut, cotton, tomato, and legumes in general (U.S. Pat. No. 5,563,055, incorporated herein by reference in its entirety).

To select or score for transformed plant cells regardless of transformation methodology, the DNA introduced into the cell contains a gene that functions in a regenerable plant tissue to produce a compound that confers upon the plant tissue resistance to an otherwise toxic compound. Genes of interest for use as a selectable, screenable, or scorable marker would include but are not limited to GUS, green fluorescent protein (GFP), luciferase (LUX), antibiotic or herbicide tolerance genes. Examples of antibiotic resistance genes include the penicillins, kanamycin, neomycin, G418, bleomycin, methotrexate (and trimethoprim), chloramphenicol, and tetracycline. Polynucleotide molecules encoding proteins involved in herbicide tolerance are known in the art, and include, but are not limited to a polynucleotide molecule encoding 5-enolpyruvylshikimate-3-phosphate synthase (EPSPS) described in U.S. Pat. No. 5,627,061, U.S. Pat. No. 5,633,435, and U.S. Pat. No. 6,040,497 and aroA described in U.S. Pat. No. 5,094,945 for glyphosate tolerance; a polynucleotide molecule encoding bromoxynil nitrilase (Bxn) described in U.S. Pat. No. 4,810,648 for Bromoxynil tolerance; a polynucleotide molecule encoding phytoene desaturase (crtI) described in Misawa et al., (*Plant J.* 4:833-840, 1993) and Misawa et al., (*Plant J.* 6:481-489, 1994) for norflurazon tolerance; a polynucleotide molecule encoding acetohydroxyacid synthase (AHAS, also known as ALS) described in Sathasiivan et al. (*Nucl. Acids Res.* 18:2188-2193, 1990) for tolerance to sulfonylurea herbicides; and the bar gene described in DeBlock, et al., (*EMBO J.* 6:2513-2519, 1987) for glufosinate and bialaphos tolerance.

The regeneration, development, and cultivation of plants from various transformed explants are well documented in the art. This regeneration and growth process typically includes the steps of selecting transformed cells and culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Cells that survive the exposure to the selective agent, or cells that have been scored positive in a screening assay, may be cultured in media that supports regeneration of plants. Developing plantlets are transferred to soil less plant growth mix, and hardened off, prior to transfer to a greenhouse or growth chamber for maturation.

The present invention can be used with any transformable cell or tissue. By transformable as used herein is meant a cell or tissue that is capable of further propagation to give rise to a plant. Those of skill in the art recognize that a number of plant cells or tissues are transformable in which after insertion of exogenous DNA and appropriate culture conditions the plant cells or tissues can form into a differentiated plant. Tissue suitable for these purposes can include but is not limited to immature embryos, scutellar tissue, suspension cell cultures, immature inflorescence, shoot meristem, nodal explants, callus tissue, hypocotyl tissue, cotyledons, roots, and leaves.

Any suitable plant culture medium can be used. Examples of suitable media would include but are not limited to MS-based media (Murashige and Skoog, Physiol. Plant, 15:473-497, 1962) or N6-based media (Chu et al., Scientia Sinica 18:659, 1975) supplemented with additional plant growth regulators including but not limited to auxins, cytokinins, ABA, and gibberellins. Those of skill in the art are familiar with the variety of tissue culture media, which when supplemented appropriately, support plant tissue growth and development and are suitable for plant transformation and regeneration. These tissue culture media can either be purchased as a commercial preparation, or custom prepared and modified. Those of skill in the art are aware that media and media supplements such as nutrients and growth regulators for use in transformation and regeneration and other culture conditions such as light intensity during incubation, pH, and incubation temperatures that can be optimized for the particular variety of interest.

One of ordinary skill will appreciate that, after an expression cassette is stably incorporated in transgenic plants and confirmed to be operable, it can be introduced into other plants by sexual crossing. Any of a number of standard breeding techniques can be used, depending upon the species to be crossed.

Identification of Plants with an Altered Phenotype

An *Arabidopsis* activation tagging screen (ACTTAG) was used to identify the association between 1) ACTTAG plant lines with an altered oil, protein and/or fiber content (see columns 4, 5 and 6 respectively, of Table 1, below) and 2) the nucleic acid sequences identified in column 3 of Tables 2 and 3, wherein each nucleic acid sequence is provided with a gene alias or a HIO designation (HIO#; see column 1 in Tables 1, 2, and 3). The HIO designation is arbitrary and does not necessarily relate to a plant having a high oil (HIO) phenotype.

Briefly, and as further described in the Examples, a large number of *Arabidopsis* plants were mutated with the pSK1015 vector, which comprises a T-DNA from the Ti plasmid of *Agrobacterium tumifaciens*, a viral enhancer element, and a selectable marker gene (Weigel et al., 2000*, Plant Physiology,* 122:1003-1013). When the T-DNA inserts into the genome of transformed plants, the enhancer element can cause up-regulation of genes in the vicinity, generally within about nine kilobases (kb) of the enhancers. T1 plants were exposed to the selective agent in order to specifically recover transformed plants that expressed the selectable marker and therefore harbored T-DNA insertions. T1 plants were allowed to grow to maturity, self-fertilize and produce seed. T2 seed was harvested, labeled and stored. To amplify the seed stocks, about eighteen T2 were sown in soil and, after germination, exposed to the selective agent to recover transformed T2 plants. T3 seed from these plants was harvested and pooled. Oil, protein and fiber content of the seed were estimated using Near Infrared Spectroscopy (NIR) as described in the Examples.

The association of a HIO nucleic acid sequence with an altered phenotype was discovered by analysis of the genomic DNA sequence flanking the T-DNA insertion in the ACTTAG line identified in column 3 of Table 1. An ACTTAG line is a family of plants derived from a single plant that was transformed with a T-DNA element containing four tandem copies of the CaMV 35S enhancers. Accordingly, the disclosed HIO nucleic acid sequences and/or polypeptides may be employed in the development of transgenic plants having an altered, for example high oil, phenotype. HIO nucleic acid sequences may be used in the generation of transgenic plants, such as oilseed crops, that provide improved oil yield from oilseed processing and result in an increase in the quantity of oil recovered from seeds of the transgenic plant. HIO nucleic acid sequences may also be used in the generation of transgenic plants, such as feed grain crops, that provide an altered phenotype resulting in increased energy for animal feeding, for example, seeds or seed meal with an altered protein and/or fiber content, resulting in an increase in AME. HIO nucleic acid sequences may further be used to increase the oil content of specialty oil crops, in order to augment yield and/or recovery of desired unusual fatty acids. Specific non-limiting examples of unusual fatty acids are ricinoleic acid, vernolic acid and the very long chain polyunsaturated fatty acids docosahexaenoic acid (DHA) and eicosapentaenoic acid (EPA). Transgenic plants that have been genetically modified to express HIO polypeptides can be used in the production of seeds, wherein the transgenic plants are grown, and oil and seed meal are obtained from plant parts (e.g. seed) using standard methods.

HIO Nucleic Acids and Polypeptides

The HIO designation for each of the HIO nucleic acid sequences discovered in the activation tagging screen described herein are listed in column 1 of Tables 1-3, below. The disclosed HIO polypeptides are listed in column 4 of Tables 2 and 3, below. The HIO designation is arbitrary and does not necessarily relate to a plant having a high oil (HIO) phenotype. As used herein, the gene alias or HIO designation refers to any polypeptide sequence (or the nucleic acid sequence that encodes it) that when expressed in a plant causes an altered phenotype in any part of the plant, for example the seeds. In one embodiment, a HIO polypeptide refers to a full-length HIO protein, or a fragment, derivative (variant), or ortholog or paralog thereof that is "functionally active," such that the protein fragment, derivative, or ortholog or paralog exhibits one or more or the functional activities associated with one or more of the disclosed full-length HIO polypeptides, for example, the amino acid sequences provided in the GenBank entry referenced in column 4 of Table 2, and 3 which correspond to the amino acid sequences set forth as SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, or SEQ ID NO: 18, or an ortholog or paralog thereof. In one preferred embodiment, a functionally active HIO polypeptide causes an altered phenotype in a transgenic plant. In another embodiment, a functionally active HIO polypeptide causes an altered oil, protein, and/or fiber content phenotype (for example, an altered seed meal content phenotype) when mis-expressed in a plant. In other preferred embodiments, mis-expression of the HIO polypeptide causes a high oil (such as, increased oil), high protein (such as, increased total protein or digestible protein), and/or low fiber (such as, decreased fiber) phenotype in a plant. In yet other preferred embodiments, mis-expression of the HIO polypeptide causes unchanged oil, high protein (such as, increased total protein or digestible protein), and/or low fiber (such as, decreased fiber) phenotype in a plant. In another embodiment, mis-expression of the HIO polypeptide causes an improved AME of meal. In yet another embodiment, a functionally active HIO polypeptide can rescue defective (including deficient) endogenous HIO polypeptide activity when expressed in a plant or in plant cells; the rescuing polypeptide may be from the same or from a different species as the species with the defective polypeptide activity. The disclosure also provides feed, meal, grain, food, or seed comprising the HIO polypeptide, or a fragment, derivative (variant), or ortholog or paralog thereof.

In another embodiment, a functionally active fragment of a full length HIO polypeptide (for example, a functionally active fragment of a native polypeptide having the amino acid sequence set forth as SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, or SEQ ID NO: 18, or a naturally occurring ortholog or paralog thereof) retains one or more of the biological properties associated with the full-length HIO polypeptide, such as signaling activity, binding activity, catalytic activity, or cellular or extra-cellular localizing activity. A HIO fragment preferably comprises a HIO domain, such as a C- or N-terminal or catalytic domain, among others, and preferably comprises at least 10, preferably at least 20, more preferably at least 25, and most preferably at least 50 contiguous amino acids of a HIO protein. Functional domains of HIO genes are listed in column 6 of Table 2 and can be identified using the PFAM program (Bateman A et al., 1999, *Nucleic Acids Res.* 27:260-262) or INTERPRO (Mulder et al., 2003, *Nucleic Acids Res.* 31, 315-318) program. Functionally active variants of full-length HIO polypeptides, or fragments thereof, include polypeptides with amino acid insertions, deletions, or substitutions that retain one of more of the biological properties associated with the full-length HIO polypeptide. In some cases, variants are generated that change the post-translational processing of an HIO polypeptide. For instance, variants may have altered protein transport or protein localization characteristics, or altered protein half-life, compared to the native polypeptide.

As used herein, the term "HIO nucleic acid" refers to any polynucleotide that when expressed in a plant causes an altered phenotype in any part of the plant, for example the seeds. In one embodiment, a HIO polynucleotide encompasses nucleic acids with the sequence provided in or complementary to the GenBank entry referenced in column 3 of Tables 2 and 3, which correspond to nucleic acid sequences set forth as SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, or SEQ ID NO: 17, as well as functionally active fragments, derivatives, or orthologs or paralogs thereof. A HIO nucleic acid of this disclosure may be DNA, derived from genomic DNA or cDNA, or RNA.

In one embodiment, a functionally active HIO nucleic acid encodes or is complementary to a nucleic acid that encodes a functionally active HIO polypeptide. A functionally active HIO nucleic acid also includes genomic DNA that serves as a template for a primary RNA transcript (i.e., an mRNA precursor) that requires processing, such as splicing, before encoding the functionally active HIO polypeptide. A HIO nucleic acid can include other non-coding sequences, which may or may not be transcribed; such sequences include 5' and 3' UTRs, polyadenylation signals and regulatory sequences that control gene expression, among others, as are known in the art. Some polypeptides require processing events, such as proteolytic cleavage, covalent modification, etc., in order to become fully active. Accordingly, functionally active nucleic acids may encode the mature or the pre-processed HIO polypeptide, or an intermediate form. A HIO polynucleotide can also include heterologous coding sequences, for example, sequences that encode a marker included to facilitate the purification of the fused polypeptide, or a transformation marker. In another embodiment, a functionally active HIO nucleic acid is capable of being used in the generation of loss-of-function HIO phenotypes, for instance, via antisense suppression, co-suppression, etc. The disclosure also provides feed, meal, grain, food, or seed comprising a nucleic acid sequence that encodes an HIO polypeptide.

In one preferred embodiment, a HIO nucleic acid used in the disclosed methods comprises a nucleic acid sequence that encodes, or is complementary to a sequence that encodes, a HIO polypeptide having at least 50%, 60%, 70%, 75%, 80%, 85%, 90%, 95%, 97%, 98%, or 99% sequence identity to a disclosed HIO polypeptide sequence, for example the amino acid sequence set forth as SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, or SEQ ID NO: 18.

In another embodiment, a HIO polypeptide comprises a polypeptide sequence with at least 50% or 60% identity to a disclosed HIO polypeptide sequence (for example, the amino acid sequence set forth as SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, or SEQ ID NO: 18) and may have at least 70%, 80%, 85%, 90%, 95%, 97%, 98%, or 99% sequence identity to a disclosed HIO polypeptide sequence. In a further embodiment, a HIO polypeptide comprises 50%, 60%, 70%, 80%, 85%, 90%, 95%, 97%, 98%, or 99% sequence identity to a disclosed HIO polypeptide sequence, and may include a conserved protein domain of the HIO polypeptide (such as the protein domain(s) listed in column 6 of Table 2). In another embodiment, a HIO polypeptide comprises a polypeptide sequence with at least 50%, 60%, 70%, 80%, 85%, 90%, 95%, 97%, 98%, or 99% sequence identity to a functionally active fragment of the polypeptide referenced in column 4 of Table 2. In yet another embodiment, a HIO polypeptide comprises a polypeptide sequence with at least 50%, 60%, 70%, 80%, 90%, 95%, 97%, 98%, or 99% identity to the polypeptide sequence of the GenBank entry referenced in column 4 of Table 2 over its entire length and comprises a conserved protein domain(s) listed in column 6 of Table 2.

In another aspect, a HIO polynucleotide sequence is at least 50% to 60% identical over its entire length to a disclosed HIO nucleic acid sequence, such as the nucleic acid sequence set forth as SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, or SEQ ID NO: 17, or nucleic acid sequences that are complementary to such a HIO sequence, and may comprise at least 70%, 80%, 85%, 90%, 95%, 97%, 98%, or 99% sequence identity to the disclosed HIO sequence, or a functionally active fragment thereof, or complementary sequences. In another embodiment, a disclosed HIO nucleic acid comprises a nucleic acid sequence as shown in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, or SEQ ID NO: 17, or nucleic acid sequences that are complementary to such a HIO sequence, and nucleic acid sequences that have substantial sequence homology to a such HIO sequences. As used herein, the phrase "substantial sequence homology" refers to those nucleic acid sequences that have slight or inconsequential sequence variations from such HIO sequences, i.e., the sequences function in substantially the same manner and encode an HIO polypeptide.

As used herein, "percent (%) sequence identity" with respect to a specified subject sequence, or a specified portion thereof, is defined as the percentage of nucleotides or amino acids in an identified sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., *J. Mol. Biol.,* 1990, 215:403-410) with search parameters set to default values. The HSP S and HSP S2 parameters are dynamic values and are established by the program itself depending upon the composition of the particular sequence and composition of the particular database against which the sequence of interest is being searched. A "percent (%) identity value" is determined by the number of matching identical nucleotides or amino acids divided by the sequence length for which the percent identity is being reported. "Percent (%) amino acid sequence similarity" is determined by performing the same calculation as for determining % amino acid sequence identity, but including conservative amino acid substitutions in addition to identical amino acids in the computation. A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine;

interchangeable basic amino acids are arginine, lysine and histidine; interchangeable acidic amino acids are aspartic acid and glutamic acid; and interchangeable small amino acids are alanine, serine, threonine, cysteine and glycine.

Derivative nucleic acid molecules of the subject nucleic acid molecules include sequences that selectively hybridize to the disclosed HIO nucleic acid sequences (for example, the nucleic acid sequence set forth as SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, or SEQ ID NO: 17). The stringency of hybridization can be controlled by temperature, ionic strength, pH, and the presence of denaturing agents such as formamide during hybridization and washing. Conditions routinely used are well known (see, e.g., *Current Protocol in Molecular Biology*, Vol. 1, Chap. 2.10, John Wiley & Sons, Publishers (1994); Sambrook et al., 1989, Molecular Cloning: A Laboratory Manual (Second Edition), Cold Spring Harbor Press, Plainview, N.Y.).

In some embodiments, a nucleic acid molecule of the disclosure is capable of hybridizing to a nucleic acid molecule containing the disclosed nucleotide sequence under stringent hybridization conditions that are: prehybridization of filters containing nucleic acid for 8 hours to overnight at 65° C. in a solution comprising 6× single strength citrate (SSC) (1×SSC is 0.15 M NaCl, 0.015 M Na citrate; pH 7.0), 5×Denhardt's solution, 0.05% sodium pyrophosphate and 100 μg/ml herring sperm DNA; hybridization for 18-20 hours at 65° C. in a solution containing 6×SSC, 1×Denhardt's solution, 100 μg/ml yeast tRNA and 0.05% sodium pyrophosphate; and washing of filters at 65° C. for 1 h in a solution containing 0.1×SSC and 0.1% SDS (sodium dodecyl sulfate). In other embodiments, moderately stringent hybridization conditions are used that are: pretreatment of filters containing nucleic acid for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 μg/ml denatured salmon sperm DNA; hybridization for 18-20 h at 40° C. in a solution containing 35% formamide, 5×SSC, 50 mM Tris-HCl (pH 7.5), 5 mM EDTA, 0.02% PVP, 0.02% Ficoll, 0.2% BSA, 100 μg/ml salmon sperm DNA, and 10% (wt/vol) dextran sulfate; followed by washing twice for 1 hour at 55° C. in a solution containing 2×SSC and 0.1% SDS. Alternatively, low stringency conditions can be used that comprise: incubation for 8 hours to overnight at 37° C. in a solution comprising 20% formamide, 5×SSC, 50 mM sodium phosphate (pH 7.6), 5×Denhardt's solution, 10% dextran sulfate, and 20 μg/ml denatured sheared salmon sperm DNA; hybridization in the same buffer for 18 to 20 hours; and washing of filters in 1×SSC at about 37° C. for 1 hour.

As a result of the degeneracy of the genetic code, a number of polynucleotide sequences encoding a HIO polypeptide can be produced. For example, codons may be selected to increase the rate at which expression of the polypeptide occurs in a particular host species, in accordance with the optimum codon usage dictated by the particular host organism (see, e.g., Nakamura et al., 1999, *Nucleic Acids Res.* 27:292). Such sequence variants may be used in the methods disclosed herein.

The disclosed methods may use orthologs (and/or paralogs) of a disclosed *Arabidopsis* HIO nucleic acid sequence. Representative putative orthologs (and/or paralogs) of each of the disclosed *Arabidopsis* HIO genes are identified in column 5 of Table 3, below. Methods of identifying the orthologs in other plant species are known in the art. In general, orthologs in different species retain the same function, due to presence of one or more protein motifs and/or 3-dimensional structures. In evolution, when a gene duplication event follows speciation, a single gene in one species, such as *Arabidopsis*, may correspond to multiple genes (paralogs) in another. When sequence data is available for a particular plant species, orthologs are generally identified by sequence homology analysis, such as BLAST analysis, usually using protein bait sequences. Sequences are assigned as a potential ortholog if the best hit sequence from the forward BLAST result retrieves the original query sequence in the reverse BLAST (Huynen M A and Bork P, 1998, *Proc. Natl. Acad. Sci.*, 95:5849-5856; Huynen M A et al., 2000, *Genome Research*, 10:1204-1210).

Programs for multiple sequence alignment, such as CLUSTAL (Thompson J D et al., 1994, *Nucleic Acids Res.* 22:4673-4680) may be used to highlight conserved regions and/or residues of homologous (orthologous and/or paralogous) proteins and to generate phylogenetic trees. In a phylogenetic tree representing multiple homologous sequences from diverse species (e.g., retrieved through BLAST analysis), orthologous sequences from two species generally appear closest on the tree with respect to all other sequences from these two species. Structural threading or other analysis of protein folding (e.g., using software by ProCeryon, Biosciences, Salzburg, Austria) may also identify potential orthologs. Nucleic acid hybridization methods may also be used to find orthologous genes and are preferred when sequence data are not available. Degenerate PCR and screening of cDNA or genomic DNA libraries are common methods for finding related gene sequences and are well known in the art (see, e.g., Sambrook, 1989, *Molecular Cloning: A Laboratory Manual* (Second Edition), Cold Spring Harbor Press, Plainview, N.Y.; Dieffenbach and Dveksler, 1995, *PCR Primer: A Laboratory Manual*, Cold Spring Harbor Laboratory Press, NY). For instance, methods for generating a cDNA library from the plant species of interest and probing the library with partially homologous gene probes are described in Sambrook et al. A highly conserved portion of the *Arabidopsis* HIO coding sequence may be used as a probe. HIO ortholog nucleic acids may hybridize to the nucleic acid of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, or SEQ ID NO: 17, under high, moderate, or low stringency conditions. After amplification or isolation of a segment of a putative ortholog, that segment may be cloned and sequenced by standard techniques and utilized as a probe to isolate a complete cDNA or genomic DNA clone.

Alternatively, it is possible to initiate an EST project to generate a database of sequence information for the plant species of interest. In another approach, antibodies that specifically bind known HIO polypeptides are used for ortholog (and/or paralog) isolation (see, e.g., Harlow and Lane, 1988, 1999, *Antibodies: A Laboratory Manual*, Cold Spring Harbor Laboratory Press, New York). Western blot analysis can determine that a HIO ortholog (i.e., a protein orthologous to a disclosed HIO polypeptide) is present in a crude extract of a particular plant species. When reactivity is observed, the sequence encoding the candidate ortholog may be isolated by screening expression libraries representing the particular plant species. Expression libraries can be constructed in a variety of commercially available vectors, including lambda gt11, as described in Sambrook, et al., 1989. Once the candidate ortholog(s) are identified by any of these means, candidate orthologous sequence are used as bait (the "query") for the reverse BLAST against sequences from *Arabidopsis* or other species in which HIO nucleic acid and/or polypeptide sequences have been identified.

HIO nucleic acids and polypeptides may be obtained using any available method. For instance, techniques for isolating cDNA or genomic DNA sequences of interest by screening DNA libraries or by using polymerase chain reaction (PCR), as previously described, are well known in the art. Alternatively, nucleic acid sequence may be synthesized. Any known method, such as site directed mutagenesis (Kunkel T A et al., 1991, *Methods Enzymol.* 204:125-39), may be used to introduce desired changes into a cloned nucleic acid.

In general, the methods disclosed herein involve incorporating the desired form of the HIO nucleic acid into a plant expression vector for transformation of plant cells, and the HIO polypeptide is expressed in the host plant. Transformed plants and plant cells expressing an HIO polypeptide express an altered phenotype and, in one specific, non-limiting example, may have high (increased) oil, high (increased) protein, and/or low (decreased) fiber content.

An "isolated" HIO nucleic acid molecule is other than in the form or setting in which it is found in nature, and is identified and separated from least one contaminant nucleic acid molecule with which it is ordinarily associated in the natural source of the HIO nucleic acid. However, an isolated HIO nucleic acid molecule includes HIO nucleic acid molecules contained in cells that ordinarily express the HIO polypeptide where, for example, the nucleic acid molecule is in a chromosomal location different from that of natural cells.

Generation of Genetically Modified Plants with an Altered Phenotype

The disclosed HIO nucleic acids and polypeptides may be used in the generation of transgenic plants having a modified or altered phenotype, for example an altered oil, protein, and/or fiber content phenotype. As used herein, an "altered oil content (phenotype)" may refer to altered oil content in any part of the plant. In a preferred embodiment, altered expression of the HIO gene in a plant is used to generate plants with a high oil content (phenotype). As used herein, an "altered total protein content (phenotype)" or an "altered digestible protein content (phenotype)" may refer to altered protein (total or digestible) content in any part of the plant. In a preferred embodiment, altered expression of the HIO gene in a plant is used to generate plants with a high (or increased) total or digestible protein content (phenotype). As used herein, an "altered fiber content (phenotype)" may refer to altered fiber content in any part of the plant. In a preferred embodiment, altered expression of the HIO gene in a plant is used to generate plants with a low (or decreased) fiber content (phenotype). The altered oil, protein and/or fiber content is often observed in seeds. Examples of a transgenic plant include plants comprising a plant transformation vector with a nucleotide sequence that encodes or is complementary to a sequence that encodes an HIO polypeptide having the amino acid sequence as set forth in SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, or SEQ ID NO: 18, or an ortholog or paralog thereof.

Transgenic plants, such as corn, soybean and canola containing the disclosed nucleic acid sequences, can be used in the production of vegetable oil and meal. Vegetable oil is used in a variety of food products, while meal from seed is used as an animal feed. After harvesting seed from transgenic plants, the seed is cleaned to remove plant stalks and other material and then flaked in roller mills to break the hulls. The crushed seed is heated to 75-100° C. to denature hydrolytic enzymes, lyse the unbroken oil containing cells, and allow small oil droplets to coalesce. Most of the oil is then removed (and can be recovered) by pressing the seed material in a screw press. The remaining oil is removed from the presscake by extraction with and organic solvents, such as hexane. The solvent is removed from the meal by heating it to approximately 100° C. After drying, the meal is then granulated to a consistent form. The meal, containing the protein, digestible carbohydrate, and fiber of the seed, may be mixed with other materials prior to being used as an animal feed.

The methods described herein for generating transgenic plants are generally applicable to all plants. Although activation tagging and gene identification is carried out in *Arabidopsis*, the HIO nucleic acid sequence (or an ortholog, paralog, variant or fragment thereof) may be expressed in any type of plant. In a preferred embodiment, oil-producing plants produce and store triacylglycerol in specific organs, primarily in seeds. Such species include soybean (*Glycine max*), rapeseed and canola (including *Brassica napus, B. campestris*), sunflower (*Helianthus annus*), cotton (*Gossypium hirsutum*), corn (*Zea mays*), cocoa (*Theobroma cacao*), safflower (*Carthamus tinctorius*), oil palm (*Elaeis guineensis*), coconut palm (*Cocos nucifera*), flax (*Linum usitatissimum*), castor (*Ricinus communis*), and peanut (*Arachis hypogaea*), as well as wheat, rice and oat. Fruit- and vegetable-bearing plants, grain-producing plants, nut-producing plants, rapid cycling *Brassica* species, alfalfa (*Medicago sativa*), tobacco (*Nicotiana*), turfgrass (Poaceae family), other forage crops, and wild species may also be a source of unique fatty acids. In other embodiments, any plant expressing the HIO nucleic acid sequence can also express increased protein and/or decreased fiber content in a specific plant part or organ, such as in seeds.

The skilled artisan will recognize that a wide variety of transformation techniques exist in the art, and new techniques are continually becoming available. Any technique that is suitable for the target host plant can be employed within the scope of the present invention. For example, the constructs can be introduced in a variety of forms including, but not limited to, as a strand of DNA, in a plasmid, or in an artificial chromosome. The introduction of the constructs into the target plant cells can be accomplished by a variety of techniques, including, but not limited to, *Agrobacterium*-mediated transformation, electroporation, microinjection, microprojectile bombardment, calcium-phosphate-DNA co-precipitation, or liposome-mediated transformation of a heterologous nucleic acid. The transformation of the plant is preferably permanent, i.e. by integration of the introduced expression constructs into the host plant genome, so that the introduced constructs are passed onto successive plant generations. Depending upon the intended use, a heterologous nucleic acid construct comprising an HIO polynucleotide may encode the entire protein or a biologically active portion thereof.

In one embodiment, binary Ti-based vector systems may be used to transfer polynucleotides. Standard *Agrobacterium* binary vectors are known to those of skill in the art, and many are commercially available (e.g., pBI121 Clontech Laboratories, Palo Alto, Calif.). A construct or vector may include a plant promoter to express the nucleic acid molecule of choice. In a preferred embodiment, the promoter is a plant promoter.

The optimal procedure for transformation of plants with *Agrobacterium* vectors will vary with the type of plant being transformed. Exemplary methods for *Agrobacterium*-mediated transformation include transformation of explants of hypocotyl, shoot tip, stem or leaf tissue, derived from sterile seedlings and/or plantlets. Such transformed plants may be reproduced sexually, or by cell or tissue culture. *Agrobacterium* transformation has been previously described for a large number of different types of plants and methods for such transformation may be found in the scientific literature. Of particular relevance are methods to transform commercially important crops, such as plants of the *Brassica* species, including canola and rapeseed, (De Block et al., 1989, *Plant Physiol,* 91:694-701), maize (Ishida et al., 1996 *Nature Biotechnol* 14:745-750, Zhang et al., 2002 *Plant Cell Rep.* 21:263-270) sunflower (Everett et al., 1987, *Bio/Technology,* 5:1201), soybean (Christou et al., 1989, *Proc. Natl. Acad. Sci. USA,* 86:7500-7504; Kline et al., 1987, *Nature,* 327:70), wheat, rice and oat.

Expression (including transcription and translation) of a HIO nucleic acid sequence may be regulated with respect to the level of expression, the tissue type(s) where expression takes place and/or developmental stage of expression. A number of heterologous regulatory sequences (e.g., promoters and enhancers) are available for controlling the expression of a HIO nucleic acid. These include constitutive, inducible and regulatable promoters, as well as promoters and enhancers that control expression in a tissue- or temporal-specific manner. Exemplary constitutive promoters include the raspberry E4 promoter (U.S. Pat. Nos. 5,783,393 and 5,783,394), the nopaline synthase (NOS) promoter (Ebert et al., *Proc. Natl. Acad. Sci.* (*U.S.A.*) 84:5745-5749, 1987), the octopine synthase (OCS) promoter (which is carried on tumor-inducing plasmids of *Agrobacterium tumefaciens*), the caulimovirus promoters such as the cauliflower mosaic virus (CaMV) 19S promoter (Lawton et al., *Plant Mol. Biol.* 9:315-324, 1987) and the CaMV 35S promoter (Odell et al., *Nature* 313:810-812, 1985 and Jones J D et al., 1992, *Transgenic Res.,* 1:285-297), the figwort mosaic virus 35S-promoter (U.S. Pat. No. 5,378,619), the light-inducible promoter from the small subunit of ribulose-1,5-bis-phosphate carboxylase (ss-RUBISCO), the Adh promoter (Walker et al., *Proc. Natl. Acad. Sci.* (*U.S.A.*) 84:6624-6628, 1987), the sucrose synthase promoter (Yang et al., *Proc. Natl. Acad. Sci.* (*U.S.A.*) 87:4144-4148, 1990), the R gene complex promoter (Chandler et al., *The Plant Cell* 1:1175-1183, 1989), the chlorophyll a/b binding protein gene promoter, the CsVMV promoter (Verdaguer B et al., 1998, *Plant Mol Biol.,* 37:1055-1067), and the melon actin promoter (published PCT application WO0056863). Exemplary tissue-specific promoters include the tomato E4 and E8 promoters (U.S. Pat. No. 5,859,330) and the tomato 2AII gene promoter (Van Haaren M J J et al., 1993, *Plant Mol. Bio.,* 21:625-640).

In one preferred embodiment, expression of the HIO nucleic acid sequence is under control of regulatory sequences from genes whose expression is associated with early seed and/or embryo development. Indeed, in a preferred embodiment, the promoter used is a seed-enhanced promoter. Examples of such promoters include the 5' regulatory regions from such genes as napin (Kridl et al., *Seed Sci. Res.* 1:209: 219, 1991), globulin (Belanger and Kriz, *Genet.,* 129: 863-872, 1991, GenBank Accession No. L22295), gamma zein Z 27 (Lopes et al., *Mol Gen Genet.,* 247:603-613, 1995), L3 oleosin promoter (U.S. Pat. No. 6,433,252), phaseolin (Bustos et al., *Plant Cell,* 1(9):839-853, 1989), arcelin5 (U.S. Application No. 2003/0046727), a soybean 7S promoter, a 7S$\alpha$ promoter (U.S. Application No. 2003/0093828), the soybean 7S$\alpha$' beta conglycinin promoter, a 7S $\alpha$' promoter (Beachy et al., *EMBO J.,* 4:3047, 1985; Schuler et al., *Nucleic Acid Res.,* 10(24):8225-8244, 1982), soybean trypsin inhibitor (Riggs et al., *Plant Cell* 1(6):609-621, 1989), ACP (Baerson et al., *Plant Mol. Biol.,* 22(2):255-267, 1993), stearoyl-ACP desaturase (Slocombe et al., *Plant Physiol.* 104(4):167-176, 1994), soybean a' subunit of $\beta$-conglycinin (Chen et al., *Proc. Natl. Acad. Sci.* 83:8560-8564, 1986), *Vicia faba* USP (P-Vf.Usp, SEQ ID NO: 1, 2, and 3 in (U.S. Application No. 2003/229918) and *Zea mays* L3 oleosin promoter (Hong et al., *Plant Mol. Biol.,* 34(3):549-555, 1997). Also included are the zeins, which are a group of storage proteins found in corn endosperm. Genomic clones for zein genes have been isolated (Pedersen et al., *Cell,* 29:1015-1026, 1982; and Russell et al., *Transgenic Res.* 6(2):157-168) and the promoters from these clones, including the 15 kD, 16 kD, 19 kD, 22 kD, 27 kD and genes, could also be used. Other promoters known to function, for example, in corn include the promoters for the following genes: waxy, Brittle, Shrunken 2, Branching enzymes I and II, starch synthases, debranching enzymes, oleosins, glutelins and sucrose synthases. Legume genes whose promoters are associated with early seed and embryo development include *V. faba legumin* (Baumlein et al., 1991, *Mol. Gen. Genet.* 225:121-8; Baumlein et al., 1992, *Plant J.* 2:233-9), *V. faba usp* (Fiedler et al., 1993, *Plant Mol. Biol.* 22:669-79), pea *convicilin* (Bown et al., 1988, *Biochem. J.* 251:717-26), pea *lectin* (dePater et al., 1993, *Plant Cell* 5:877-86), *P. vulgaris* beta phaseolin (Bustos et al., 1991, *EMBO J.* 10: 1469-79), *P. vulgaris* DLEC2 and PHS [beta] (Bobb et al., 1997, *Nucleic Acids Res.* 25:641-7), and soybean beta-Conglycinin, 7S storage protein (Chamberland et al., 1992, *Plant Mol. Biol.* 19:937-49).

Cereal genes whose promoters are associated with early seed and embryo development include rice glutelin ("GluA-3," Yoshihara and Takaiwa, 1996, *Plant Cell Physiol* 37:107-11; "GluB-1," Takaiwa et al., 1996, *Plant Mol. Biol.* 30:1207-21; Washida et al., 1999, *Plant Mol. Biol.* 40:1-12; "Gt3," Leisy et al., 1990, *Plant Mol. Biol.* 14:41-50), rice prolamin (Zhou & Fan, 1993, *Transgenic Res.* 2:141-6), wheat prolamin (Hammond-Kosack et al., 1993, *EMBO J.* 12:545-54), maize zein (Z4, Matzke et al., 1990, *Plant Mol. Biol.* 14:323-32), and barley B-hordeins (Entwistle et al., 1991, *Plant Mol. Biol.* 17:1217-31).

Other genes whose promoters are associated with early seed and embryo development include oil palm GLO7A (7S globulin, Morcillo et al., 2001, *Physiol. Plant* 112:233-243), *Brassica napus* napin, 2S storage protein, and napA gene (Josefsson et al., 1987, *J. Biol. Chem.* 262:12196-201; Stalberg et al., 1993, *Plant Mol. Biol.* 1993 23:671-83; Ellerstrom et al., 1996, *Plant Mol. Biol.* 32:1019-27), *Brassica napus oleosin* (Keddie et al., 1994, *Plant Mol. Biol.* 24:327-40), *Arabidopsis oleosin* (Plant et al., 1994, *Plant Mol. Biol.* 25:193-205), *Arabidopsis* FAE1 (Rossak et al., 2001, *Plant Mol. Biol.* 46:717-25), *Canavalia gladiata* conA (Yamamoto et al., 1995, *Plant Mol. Biol.* 27:729-41), and *Catharanthus roseus* strictosidine synthase (Str, Ouwerkerk and Memelink, 1999, *Mol. Gen. Genet.* 261:635-43). In another preferred embodiment, regulatory sequences from genes expressed during oil biosynthesis are used (see, e.g., U.S. Pat. No. 5,952,544). Alternative promoters are from plant storage protein genes (Bevan et al., 1993, *Philos. Trans. R. Soc. Lond. B. Biol. Sci.* 342:209-15). Additional promoters that may be utilized are described, for example, in U.S. Pat. Nos. 5,378, 619; 5,391,725; 5,428,147; 5,447,858; 5,608,144; 5,608,144; 5,614,399; 5,633,441; 5,633,435; and 4,633,436.

In another embodiment, the endogenous HIO gene may be placed under the control of a transgenic transcription factor or used to design binding sites that modulates its expression. One such class of transcription factors are the $Cys_2$-$His_2$-zinc finger proteins (ZFPs). ZFPs are common DNA binding proteins and can be designed to specifically bind to specific DNA sequences (Beerli & Barbas, Nat. Biotechnol., 2002, 20:135-141.; Gommans et al., J Mol Biol., 2005, 354:507-519). Individual zinc-finger domains are composed of approximately 30 amino acids, are structurally conserved and can interact with 3-4 bp of DNA. A polypeptide containing multiple zinc-fingers designed to bind to a specific DNA sequence in the promoter of a HIO gene can be synthesized. The principles for designing the zinc finger domains to interact with specific DNA sequences have been described in Segal et al., (Segal et al., Proc Natl Acad Sci USA., 1999, 96:2758-2763), Dreier et al. (Dreier et al., J Mol Biol., 2000, 303:489-502), and Beerli and Barbas (Beerli & Barbas, Nat. Biotechnol., 2002, 20:135-141). These DNA binding domains may be fused to effector domains to form a synthetic ZFP that may regulate transcription of genes to which they bind. Effector domains that can activate transcription include but are not limited to the acidic portion of the herpes simplex virus protein VP16 (Sadowski et al., Nature., 1988, 335:563-564) and VP64 (Beerli et al., Proc Natl Acad Sci USA., 1998, 95:14628-14633), and the NF-κB transcription factor p65 domain (Bae et al., Nat Biotechnol., 2003, 21:275-280., Liu et al., J Biol Chem., 2001, 276:11323-11334). Effector domains that can repress transcription include but are not limited to mSIN3 and KRAB (Ayer et al., Mol Cell Biol., 1996, 16:5772-5781, Beerli & Barbas, Nat Biotechnol., 2002, 20:135-141, Beerli et al., Proc Natl Acad Sci USA, 1998, 95:14628-14633, Margolin et al., Proc Natl Acad Sci USA., 1994, 91:4509-4513). These approaches have been shown to work in plants (Guan et al., Proc Natl Acad Sci USA., 2002, 99:13296-13301, Stege et al., Plant J., 2002, 32:1077-1086, Van Eenennaam et al., Metab Eng., 2004, 6:101-108).

In yet another aspect, in some cases it may be desirable to inhibit the expression of the endogenous HIO nucleic acid sequence in a host cell. Exemplary methods for practicing this aspect of the invention include, but are not limited to antisense suppression (Smith, et al., 1988, *Nature,* 334:724-726; van der Krol et al., 1988, *BioTechniques,* 6:958-976); co-suppression (Napoli, et al., 1990, *Plant Cell,* 2:279-289); ribozymes (PCT Publication WO 97/10328); and combinations of sense and antisense (Waterhouse, et al., 1998, *Proc. Natl. Acad. Sci. USA,* 95:13959-13964). Methods for the suppression of endogenous sequences in a host cell typically employ the transcription or transcription and translation of at least a portion of the sequence to be suppressed. Such sequences may be homologous to coding as well as non-coding regions of the endogenous sequence. Antisense inhibition may use the entire cDNA sequence (Sheehy et al., 1988, *Proc. Natl. Acad. Sci. USA,* 85:8805-8809), a partial cDNA sequence including fragments of 5' coding sequence, (Cannon et al., 1990, *Plant Mol. Biol.,* 15:39-47), or 3' non-coding sequences (Ch'ng et al., 1989, *Proc. Natl. Acad. Sci. USA,* 86:10006-10010). Cosuppression techniques may use the entire cDNA sequence (Napoli et al., 1990, *Plant Cell,* 2:279-289; van der Krol et al., 1990, *Plant Cell,* 2:291-299), or a partial cDNA sequence (Smith et al., 1990, *Mol. Gen. Genetics,* 224:477-481).

Standard molecular and genetic tests may be performed to further analyze the association between a nucleic acid sequence and an observed phenotype. Exemplary techniques are described below.

1. DNA/RNA Analysis

The stage- and tissue-specific gene expression patterns in mutant versus wild-type lines may be determined, for instance, by in situ hybridization. Analysis of the methylation status of the gene, especially flanking regulatory regions, may be performed. Other suitable techniques include over-expression, ectopic expression, expression in other plant species and gene knock-out (reverse genetics, targeted knock-out, viral induced gene silencing (VIGS; see, Baulcombe D, 1999, *Arch. Virol. Suppl.* 15:189-201).

In a preferred application expression profiling, generally by microarray analysis, is used to simultaneously measure differences or induced changes in the expression of many different genes. Techniques for microarray analysis are well known in the art (Schena M et al., *Science* 1995 270:467-470; Baldwin D et al., 1999, *Cur. Opin. Plant Biol.* 2(2):96-103; Dangond F, *Physiol Genomics* (2000) 2:53-58; van Hal N L et al., *J Biotechnol.* (2000) 78:271-280; Richmond T and Somerville S, *Curr. Opin. Plant Biol.* 2000 3:108-116). Expression profiling of individual tagged lines may be performed. Such analysis can identify other genes that are coordinately regulated as a consequence of the over-expression of the gene of interest, which may help to place an unknown gene in a particular pathway.

2. Gene Product Analysis

Analysis of gene products may include recombinant protein expression, antisera production, immunolocalization, biochemical assays for catalytic or other activity, analysis of phosphorylation status, and analysis of interaction with other proteins via yeast two-hybrid assays.

3. Pathway Analysis

Pathway analysis may include placing a gene or gene product within a particular biochemical, metabolic or signaling pathway based on its mis-expression phenotype or by sequence homology with related genes. Alternatively, analysis may comprise genetic crosses with wild-type lines and other mutant lines (creating double mutants) to order the gene in a pathway, or determining the effect of a mutation on expression of downstream "reporter" genes in a pathway.

Generation of Mutated Plants with an Altered Phenotype

Additional methods are disclosed herein of generating a plant having an altered phenotype, wherein a plant is identified that has a mutation or an allele in its HIO nucleic acid sequence that results in an altered phenotype, compared to plants lacking the mutation or allele. The mutated plant can be generated using one or more mutagens, for example a chemical mutagen (such as ethylmethane sulfonate, methyl methane sulfonate, diethylsulfate, and nitrosoguanidine, or 5-bromo-deoxyuridine) radiation, or ultraviolet light. In some embodiments of the method, the mutated plant can be bred to generate progeny, which inherit the mutation or allele and have an altered phenotype. For example, provided herein is a method of identifying plants that have one or more mutations in the endogenous HIO nucleic acid sequence that confer an altered phenotype and generating progeny of these mutated plants having such a phenotype that are not transgenic. The mutated plants with an altered phenotype can have an altered oil, protein, and/or fiber content, or an altered seed meal content.

In one specific embodiment of the method, called "TILLING" (for targeting induced local lesions in genomes), mutations are induced in the seed of a plant of interest, for example, using EMS (ethylmethane sulfonate) treatment. The resulting plants are grown and self-fertilized, and the progeny are used to prepare DNA samples. PCR amplification and sequencing of the HIO nucleic acid sequence is used to identify whether a mutated plant has a mutation in the HIO nucleic acid sequence. Plants having HIO mutations may then be tested for altered oil, protein, and/or fiber content. To confirm that the HIO mutation causes the modified phenotype, experiments correlating the presence of the modified gene and the modified phenotype through genetic crosses can be performed. TILLING can identify mutations that alter the expression of specific genes or the activity of proteins encoded by these genes (see Colbert et al., 2001, *Plant Physiol.* 126:480-484; McCallum et al., 2000, *Nature Biotechnology* 18:455-457).

In another specific embodiment of the method, a candidate gene/Quantitative Trait Locus (QTLs) approach can be used in a marker-assisted breeding program to identify alleles of or mutations in the HIO nucleic acid sequence or orthologs (and/or paralogs) of the HIO nucleic acid sequence that may confer altered oil, protein, and/or fiber content (see Bert et al., *Theor Appl Genet.,* 2003 June; 107(1):181-9; and Lionneton et al., *Genome,* 2002 December; 45(6):1203-15). Thus, in a further aspect of the disclosure, a HIO nucleic acid is used to identify whether a plant having altered oil, protein, and/or fiber content has a mutation in an endogenous HIO nucleic acid sequence or has a particular allele that causes altered oil, protein, and/or fiber content in the plant.

While the disclosure has been described with reference to specific methods and embodiments, it will be appreciated that various modifications and changes may be made without departing from the disclosure. All publications cited herein are expressly incorporated herein by reference for the purpose of describing and disclosing compositions and methodologies that might be used in connection with the disclosure. All cited patents, patent applications, and sequence information in referenced public databases are also incorporated by reference.

EXAMPLES

Example 1

Generation of Plants with a HIO Phenotype by Transformation with an Activation Tagging Construct This Example describes the generation of transgenic plants with altered oil, protein, and/or fiber content.

Mutants were generated using the activation tagging "ACTTAG" vector, pSK1015 (GI#6537289; Weigel D et al., 2000, *Plant Physiology,* 122:1003-1013). Standard methods were used for the generation of *Arabidopsis* transgenic plants, and were essentially as described in published application PCT WO0183697. Briefly, T0 *Arabidopsis* (Col-0) plants were transformed with *Agrobacterium* carrying the pSK1015 vector, which comprises T-DNA derived from the *Agrobacterium* Ti plasmid, an herbicide resistance selectable marker gene, and the 4× CaMV 35S enhancer element. Transgenic plants were selected at the T1 generation based on herbicide resistance. T2 seed (from T1 plants) was harvested and sown in soil. T2 plants were exposed to the herbicide to kill plants lacking the ACTTAG vector. T2 plants were grown to maturity, allowed to self-fertilize and set seed. T3 seed (from the T2 plants) was harvested in bulk for each line.

T3 seed was analyzed by Near Infrared Spectroscopy (NIR) at the time of harvest. NIR spectra were captured using a Bruker 22 near infrared spectrometer. Bruker Software was used to estimate total seed oil, total seed protein and total seed fiber content using data from NIR analysis and reference methods according to the manufacturer's instructions. Oil content predicting calibrations were developed following the general method of AOCS Procedure Am1-92, Official Methods and Recommended Practices of the American Oil Chemists Society, 5th Ed., AOCS, Champaign, Ill. A NIR total protein content predicting calibration was developed using total nitrogen content data of seed samples following the general method of Dumas Procedure AOAC 968.06 (Official Methods of Analysis of AOAC International 17$^{th}$ Edition AOAC, Gaithersburg, Md.). A NIR fiber content predicting calibration was developed using crude fiber content data of seed samples following the general method of AOAC Official Method 962.09 (Official Methods of Analysis of AOAC International 17$^{th}$ Edition AOAC, Gaithersburg, Md.). A NIR oleic acid content predicting calibration was developed using oleic acid content data of seed samples determined by following the method of Browse et al. (1986 Anal. Biochem. 152:141-145). A NIR calibration curve for predicting digestible protein content was developed by measuring digestible protein content in a set of seed samples. Total protein content of in a known mass of seed was determined by measuring the total nitrogen content of the seed using the Dumas method (AOAC Official Method 968.06). The seed fiber is extracted from a separate seed sample using the method of Honig and Rackis, (1979, *J. Agri. Food Chem.,* 27: 1262-1266). The undigested protein remaining associated with the fiber is measured by the Dumas method (AOAC Official Method 968.06). Digestible protein content is determined by subtracting the amount of undigested protein associated with the fiber from the total amount of protein in the seed.

Oil, protein and fiber predictions from NIR spectra were compared for 82,274 individual ACTTAG lines. Subsequent to seed compositional analysis, the position of the ACTTAG element in the genome in each line was determined by inverse PCR and sequencing. 37,995 lines with recovered flanking sequences were considered in this analysis.

Seed oil, and protein values in 82,274 lines were determined by NIR spectroscopy and normalized to allow comparison of seed component values in plants grown at different times. Oil, protein and fiber values were normalized by calculating the average oil, protein and fiber values in seed from all plants planted on the same day (including a large number of other ACTTAG plants, including control, wild-type, or non-transgenic plants). The seed components for each line was expressed as a "percent relative value" which was calculated by dividing the component value for each line with the average component value for all lines planted on the same day (which should approximate the value in control, wild-type, or non-transgenic plants). The "percent relative protein" and "percent relative fiber" were calculated similarly.

Inverse PCR was used to recover genomic DNA flanking the T-DNA insertion. The PCR product was subjected to sequence analysis and placed on the genome using a basic BLASTN search and/or a search of the *Arabidopsis* Information Resource (TAIR) database (available at the publicly available website). Generally, promoters within 9 kb of the enhancers in the ACTTAG element are considered to be within "activation space." Genes with T-DNA inserts within coding sequences were not considered to be within "activation space." The ACTTAG lines identified are listed in column 3 of Table 1. In some cases more than one ACTTAG line is associated with a gene. The relative oil, protein, fiber and oleic acid values in columns 4, 5, 6 and 7, respectively, are determined by comparing the seed component in the plant identified in column 3 relative to other plants grown at the same time and not displaying the trait.

TABLE 1

| 1. Alias | 2. TAIR ID | 3. Plant ID | 4. Relative Oil (%) | 5. Relative Protein (%) | 6. Relative Fiber (%) | 7. Relative Oleic Acid |
|---|---|---|---|---|---|---|
| HIO2102 E | At5g54030 | IN067852 | 110.61 | 96 | 107.13 | 110.12 |
| HIO2055 B | At3g44700 | IN081592 | 116.83 | 90.28 | 102.39 | 167.31 |
| HIO2055 B | At3g44700 | IN063007 | 109.58 | 94.35 | 109.97 | 122.15 |
| HIO2065 A | At3g48660 | IN063482 | 111.58 | 103.49 | 107.6 | 114.09 |

TABLE 1-continued

| 1. Alias | 2. TAIR ID | 3. Plant ID | 4. Relative Oil (%) | 5. Relative Protein (%) | 6. Relative Fiber (%) | 7. Relative Oleic Acid |
|---|---|---|---|---|---|---|
| HIO2065 A | At3g48660 | IN075786 | 111.18 | 89.8 | 104.34 | 104.2 |
| HIO2087 A | At2g40970 | IN061969 | 113.48 | 96.53 | 91.01 | 114.88 |
| HIO2087 A | At2g40970 | IN090716 | 113.79 | 87.02 | 108.42 | 127.69 |
| HIO2047 A | At3g60120 | IN083533 | 128.33 | 83.38 | 101.58 | 136.88 |
| HIO2047 A | At3g60120 | IN046624 | 104.99 | 99.76 | 105.16 | 92.37 |
| HIO2047 B | At3g60130 | IN083533 | 128.33 | 83.38 | 101.58 | 136.88 |
| HIO2047 B | At3g60130 | IN046624 | 104.99 | 99.76 | 105.16 | 92.37 |
| HIO2069 B | At1g48850 | IN023797 | 110.84 | 93.97 | 87.87 | 98 |
| HIO2069 B | At1g48850 | IN071328 | 109.18 | 93.49 | 100.74 | 120.77 |
| HIO2082 A | At4g23600 | IN066431 | 117.93 | 92.05 | 102.06 | 113.39 |
| HIO2082 A | At4g23600 | IN011312 | 111.39 | 91.3 | 99.43 | 102.13 |

TABLE 2

| 1. Locus | 2. Tair ID | 3. Nucleic Acid seq. GI# | 4. Polypeptide seq. GI# | 5. Putative biochemical function/protein name | 6. Conserved protein domain |
|---|---|---|---|---|---|
| HIO2102 E | At5g54030 | gi\|18423581 | gi\|15239527 | DC1 domain-containing protein | IPR011424 C1-like |
| | | | | | IPR004146 DC1 |
| | | | | | IPR002219 Protein kinase C, phorbol ester/diacylglycerol binding |
| HIO2055 B | At3g44700 | gi\|18407832 | gi\|15230485 | expressed protein | IPR004158 Plant protein of unknown function |
| HIO2065 A | At3g48660 | gi\|18408676 | gi\|15228422 | hypothetical protein | |
| HIO2087 A | At2g40970 | gi\|30688486 | gi\|15226794 | myb family transcription factor | IPR001005 Myb, DNA-binding |
| | | | | | IPR006447 Myb-like DNA-binding region, SHAQKYF class |
| HIO2047 A | At3g60120 | gi\|18411486 | gi\|15232260 | glycosyl hydrolase family 1 protein | IPR001360 Glycoside hydrolase, family 1 |
| | | | | | IPR005928 6-phospho-beta-galactosidase |
| HIO2047 B | At3g60130 | gi\|42566081 | gi\|15232261 | glycosyl hydrolase family 1 protein/beta-glucosidase, putative (YLS1) | IPR001360 Glycoside hydrolase, family 1 |
| | | | | | IPR005928 6-phospho-beta-galactosidase |
| HIO2069 B | At1g48850 | gi\|42562617 | gi\|18402389 | chorismate synthase, putative/5-enolpyruvylshikimate-3-phosphate pho | IPR000453 Chorismate synthase |
| HIO2082 A | At4g23600 | GI: 30686249 | GI: 15236533 | coronatine-responsive tyrosine aminotransferase/tyrosine transaminase | IPR004839 Aminotransferase, class I and II |
| | | | | | IPR001176 1-aminocyclopropane-1-carboxylate synthase |
| | | | | | IPR005860 L-threonine-O-3-phosphate decarboxylase |
| | | | | | IPR005958 Tyrosine/nicotianamine aminotransferase |
| | | | | | IPR005957 Animal tyrosine aminotransferase |
| | | | | | IPR005861 Histidinol-phosphate aminotransferase |

TABLE 2-continued

| 1. Locus | 2. Tair ID | 3. Nucleic Acid seq. GI# | 4. Polypeptide seq. GI# | 5. Putative biochemical function/protein name | 6. Conserved protein domain |
|---|---|---|---|---|---|
| HIO2082 A | At4g23600 | gi\|42570154 | gi\|30686253 | coronatine-responsive tyrosine aminotransferase/ tyrosine transaminase | IPR004839 Aminotransferase, class I and II |
| | | | | | IPR001176 1-aminocyclopropane-1-carboxylate synthase IPR005860 L-threonine-O-3-phosphate decarboxylase IPR005958 Tyrosine/nicotianamine aminotransferase IPR005957 Animal tyrosine aminotransferase IPR005861 Histidinol-phosphate aminotransferase |

TABLE 3

| 1. Locus | 2. Tair ID | 3. Nucleic Acid seq. GI# | 4. Polypeptide seq. GI# | 5. Orthologs Nucleic Acid GI# | Polypeptide GI# | Species |
|---|---|---|---|---|---|---|
| HIO2102 E | At5g54030 | gi\|18423581 | gi\|15239527 | GI: 18423582 | gi\|15239528 | *Arabidopsis thaliana* |
| | | | | GI: 42568520 | gi\|42568521 | *Arabidopsis thaliana* |
| | | | | GI: 42570547 | gi\|42570548 | *Arabidopsis thaliana* |
| HIO2055 B | At3g44700 | gi\|18407832 | gi\|15230485 | gi\|30692250 | gi\|15230487 | *Arabidopsis thaliana* |
| | | | | gi\|42573448 | gi\|42573449 | *Arabidopsis thaliana* |
| | | | | gi\|42568013 | gi\|15242911 | *Arabidopsis thaliana* |
| HIO2065 A | At3g48660 | gi\|18408676 | gi\|15228422 | gi\|33327287 | gi\|33327288 | *Phaseolus vulgaris* |
| | | | | gi\|30697855 | gi\|15242790 | *Arabidopsis thaliana* |
| | | | | gi\|51964055 | gi\|51964056 | *Oryza sativa* (*japonica* cultivar-group) |
| | | | | GI: 50908834 | GI: 50908835 | *Oryza sativa* (*japonica* cultivar-group) |
| HIO2087 A | At2g40970 | gi\|30688486 | gi\|15226794 | gi\|42563989 | gi\|15228370 | *Arabidopsis thaliana* |
| | | | | gi\|30680790 | gi\|15238416 | *Arabidopsis thaliana* |
| | | | | gi\|44804357 | gi\|51038221 | *Oryza sativa* (*japonica* cultivar-group) |
| HIO2047 A | At3g60120 | gi\|18411486 | gi\|15232260 | gi\|30689729 | gi\|15224886 | *Arabidopsis thaliana* |
| | | | | gi\|30695132 | gi\|15232262 | *Arabidopsis thaliana* |
| | | | | gi\|18420805 | gi\|15238569 | *Arabidopsis thaliana* |
| HIO2047 B | At3g60130 | gi\|42566081 | gi\|15232261 | gi\|18422464 | gi\|15241543 | *Arabidopsis thaliana* |
| | | | | gi\|18422191 | gi\|15238331 | *Arabidopsis thaliana* |

TABLE 3-continued

| 1. Locus | 2. Tair ID | 3. Nucleic Acid seq. GI# | 4. Polypeptide seq. GI# | 5. Orthologs Nucleic Acid GI# | Polypeptide GI# | Species |
|---|---|---|---|---|---|---|
| | | | | gi\|18406539 | gi\|15224879 | *Arabidopsis thaliana* |
| HIO2069 B | At1g48850 | gi\|42562617 | gi\|18402389 | gi\|410481 | gi\|410482 | *Lycopersicon esculentum* |
| | | | | gi\|18255 | gi\|18256 | *Corydalis sempervirens* |
| | | | | gi\|410483 | gi\|410484 | *Lycopersicon esculentum* |
| HIO2082 A | At4g23600 | GI: 30686249 | GI: 15236533 | gi\|28192641 | gi\|28192642 | *Brassica oleracea* |
| | | | | gi\|30686247 | gi\|22328891 | *Arabidopsis thaliana* |
| | | | | gi\|42570154 | gi\|30686253 | *Arabidopsis thaliana* |
| HIO2082 A | At4g23600 | gi\|42570154 | gi\|30686253 | gi\|30686249 | gi\|15236533 | *Arabidopsis thaliana* |
| | | | | gi\|28192641 | gi\|28192642 | *Brassica oleracea* |
| | | | | gi\|30686247 | gi\|22328891 | *Arabidopsis thaliana* |

Example 2

Analysis of the *Arabidopsis* HIO Sequence

Sequence analyses were performed with BLAST (Altschul et al., 1990, *J. Mol. Biol.* 215:403-410), PFAM (Bateman et al., 1999, *Nucleic Acids Res.* 27:260-262), INTERPRO (Mulder et al. 2003 *Nucleic Acids Res.* 31, 315-318), PSORT (Nakai K, and Horton P, 1999, *Trends Biochem. Sci.* 24:34-6), and/or CLUSTAL (Thompson J D et al., 1994, *Nucleic Acids Res.* 22:4673-4680).

Example 3

Recapitulation Experiments

To test whether over-expression of the genes in Tables 1 and 2 alter the seed composition phenotype, protein, digestible protein, oil and fiber content in seeds from transgenic plants expressing these genes was compared with protein, digestible protein, oil and fiber content in seeds from non-transgenic control plants. To do this, the genes were cloned into plant transformation vectors behind the strong constitutive CsVMV promoter and the seed specific PRU promoter. These constructs were transformed into *Arabidopsis* plants using the floral dip method. The plant transformation vector contains a gene, which provides resistance to a toxic compound, and serves as a selectable marker. Seed from the transformed plants were plated on agar medium containing the toxic compound. After 7 days, transgenic plants were identified as healthy green plants and transplanted to soil. Non-transgenic control plants were germinated on agar medium, allowed to grow for 7 days and then transplanted to soil. Transgenic seedlings and non-transgenic control plants were transplanted to two inch pots that were placed in random positions in a 10 inch by 20 inch tray. The plants were grown to maturity, allowed to self-fertilize and set seed. Seed was harvested from each plant and its oil content estimated by Near Infrared (NIR) Spectroscopy using methods previously described. The effect of each construct on seed composition was examined in at least two experiments.

Table 4 lists constructs tested for causing a significant increase in oil, protein, digestible protein or a significant decrease in fiber were identified by a two-way Analysis of Variance (ANOVA) test at a p-value ≦0.05. These constructs are listed in Table 4. The ANOVA p-values for Protein, Oil, Digestible Protein and Fiber are listed in columns 4-7, respectively. Those with a significant p-value are listed in bold. The Average values for Protein, Oil, Digestible Protein and Fiber are listed in columns 8-11, respectively and were calculated by averaging the average values determined for the transgenic plants in each experiment.

TABLE 4

| Alias | Tair | Construct | ANOVA Protein | ANOVA Oil | ANOVA Digestible Protein | ANOVA Fiber | Average Protein | Average Oil | Average Digestible Protein | Average Fiber |
|---|---|---|---|---|---|---|---|---|---|---|
| HIO2102 E | At5g54030 | Pru::At5g54030 | **0.001** | **0.013** | **0.000** | **0.003** | 104.7 | 97.2 | 102.1 | 97.5 |
| HIO2055 B | At3g44700 | Pru::At3g44700 | **0.007** | **0.024** | **0.001** | **0.001** | 107.7 | 97.7 | 102.8 | 94.7 |
| HIO2065 A | At3g48660 | Pru::At3g48660 | **0.046** | 0.076 | **0.019** | **0.004** | 104.4 | 97.7 | 102.7 | 97.2 |
| HIO2087 A | At2g40970 | CsVMV::At2g40970 | **0.049** | 0.868 | **0.000** | **0.001** | 102.8 | 100.3 | 103.5 | 96.1 |
| HIO2047 B | At3g60130 | Pru::At3g60130 | **0.019** | 0.265 | **0.000** | **0.003** | 105.3 | 98.2 | 104.7 | 94.7 |
| HIO2047 A | At3g60120 | CsVMV::At3g60120 | **0.001** | 0.081 | **0.046** | **0.000** | 105.4 | 98.0 | 101.6 | 95.3 |
| HIO2069 B | At1g48850 | CsVMV::At1g48850 | **0.002** | **0.000** | **0.000** | **0.002** | 107.7 | 88.6 | 107.0 | 96.7 |
| HIO2082 A | At4g23600 | CsVMV::At4g23600 | **0.034** | 0.229 | **0.012** | **0.001** | 104.1 | 98.6 | 102.4 | 97.2 |

It is claimed:

1. A transgenic plant, comprising a plant transformation vector comprising a nucleotide sequence that encodes an HIO polypeptide comprising an amino acid sequence at least 95% identical to the amino acid sequence as set forth in SEQ ID NO: 2, whereby the transgenic plant has an increased oil content phenotype or an increased meal quality phenotype, relative to control plants.

2. The transgenic plant of claim 1, which is selected from the group consisting of plants of the *Brassica* species, including canola and rapeseed, soy, corn, sunflower, cotton, cocoa, safflower, oil palm, coconut palm, flax, castor, peanut, wheat, oat, and rice.

3. A plant part obtained from the plant according to claim 1.

4. The plant part of claim 3, which is a seed.

5. Meal, feed, or food produced from the seed of claim 4.

6. A method of producing oil comprising growing the transgenic plant of claim 1 and recovering oil from said plant.

7. The method of claim 6, wherein the oil is recovered from a seed of the plant.

8. A feed, meal, grain, food, or seed from the transgenic plant of claim 1, wherein the feed, meal, grain, food, or seed comprises a polypeptide encoded by the nucleic acid sequence as set forth in SEQ ID NO: 1.

9. A feed, meal, grain, food, or seed from the transgenic plant of claim 1, wherein the feed, meal, grain, food, or seed comprises a polypeptide comprising the amino acid sequence as set forth in SEQ ID NO: 2 or a polypeptide comprising an amino acid sequence at least 95% identical to the amino acid sequence as set forth in SEQ ID NO: 2.

10. The transgenic plant of claim 1, wherein an increased meal quality phenotype comprises an increase in available metabolizable energy in meal produced from seeds of the transgenic plant, relative to control plants.

11. The transgenic plant of claim 10, wherein an increase in available metabolizable energy comprises an altered protein and/or fiber content in the seeds of the transgenic plant.

12. The transgenic plant of claim 11, wherein the protein content is increased and/or the fiber content is decreased.

13. The transgenic plant of claim 10, wherein an increase in available metabolizable energy comprises a decreased fiber content in the seeds of the transgenic plant.

14. A method of producing meal, comprising growing the transgenic plant of claim 1, and recovering meal from the plant, thereby producing meal.

15. The method of claim 14, wherein the meal is produced from seeds of the plant.

16. A method of producing increased oil content in a plant, said method comprising:

a) introducing into progenitor cells of the plant a plant transformation vector comprising a nucleotide sequence that encodes a HIO polypeptide comprising an amino acid sequence at least 95% identical to the amino acid sequence as set forth in SEQ ID NO: 2, and b) growing the transformed progenitor cells to produce a transgenic plant, wherein said polynucleotide sequence is expressed, and said transgenic plant exhibits an increased oil content phenotype relative to control plants.

17. A plant obtained by a method of claim 16.

18. The plant of claim 17, which is selected from the group consisting of plants of the *Brassica* species, including canola and rapeseed, soy, corn, sunflower, cotton, cocoa, safflower, oil palm, coconut palm, flax, castor, peanut, wheat, oat, and rice.

19. The plant of claim 17, wherein the plant is selected from the group consisting of a plant grown from said progenitor cells, a plant that is the direct progeny of a plant grown from said progenitor cells, and a plant that is the indirect progeny of a plant grown from said progenitor cells.

20. A method of producing an improved meal quality phenotype in a plant, said method comprising:

a) introducing into progenitor cells of the plant a plant transformation vector comprising a nucleotide sequence that encodes an HIO polypeptide comprising an amino acid sequence at least 95% identical to the amino acid sequence set forth in SEQ ID NO: 2, and b) growing the transformed progenitor cells to produce a transgenic plant, wherein the nucleotide sequence is expressed, and the transgenic plant exhibits an increased meal quality phenotype relative to control plants, thereby producing the improved meal quality phenotype in the plant.

21. A plant obtained by a method of claim 20.

22. The plant of claim 21, which is selected from the group consisting of plants of the *Brassica* species, including canola and rapeseed, soy, corn, sunflower, cotton, cocoa, safflower, oil palm, coconut palm, flax, castor, peanut, wheat, oat, and rice.

23. The plant of claim 21, wherein the plant is selected from the group consisting of a plant grown from said progenitor cells, a plant that is the direct progeny of a plant grown from said progenitor cells, and a plant that is the indirect progeny of a plant grown from said progenitor cells.

24. The feed, meal, grain, food, or seed of claim 9, wherein the polypeptide comprises the amino acid sequence as set forth in SEQ ID NO: 2.

* * * * *

UNITED STATES PATENT AND TRADEMARK OFFICE

CERTIFICATE OF CORRECTION

PATENT NO. : 7,790,954 B2
APPLICATION NO. : 11/958113
DATED : September 7, 2010
INVENTOR(S) : Davies and Ng It is certified that error appears in the above-identified patent and that said Letters Patent is hereby corrected as shown below:

In the Specification:

Column 13, line 22, "pSK1015" should read --pSKI015--.

Column 25, line 32, "pSK1015" should read --pSKI015--.

Column 25, line 37, "pSK1015" should read --pSKI015--.

Signed and Sealed this
Thirteenth Day of September, 2011

David J. Kappos

David J. Kappos
*Director of the United States Patent and Trademark Office*

SEQUENCE LISTING

<160> NUMBER OF SEQ ID NOS: 18

<210> SEQ ID NO 1
<211> LENGTH: 1260
<212> TYPE: DNA
<213> ORGANISM: Arabidopsis Thaliana

<400> SEQUENCE: 1

```
atgtcttcta ctgatgattt cgaagtggaa accatatctg aaatcatggt tccgtttcat      60
catcatcctt tatcaagtta tgcttctgaa tttttgactt cttgctcttt gtgccttttc     120
tctacgtttc taggagaaat agtcactcgc atcagatatc agtgtatgga ttgcggcttg     180
aagttacacg acgaatgcat caacagcctt tccctcaacc gaccctttct gtgcaatcac     240
attctcaagg tgtatactca tattttcaca tcatctggcc gtatatatga aaacacttgt     300
catttttgtc aaagtaagtt agaattttta tttgctcgtt gcactatatg caacttaaac     360
gtggatatag aatgtttgtt tgcactgcca ccactcacaa tttctgaacc aaaacaccac     420
aagcatagcc tcagtctcct gctaaggcta gtcaccttta cttgtaatgc ttgtggtgtg     480
gaaggcgacc gcaatcctta cgtatgtctt gaatgcaatc tgatggtcca caaagattgt     540
gttgagaatc taccgcgagt cataagcata aatcggcatg accatcgcat atctcatact     600
tttcatcttg gtaaaaaaga aggagattgg gagtgtggag tttgtcggaa gatgattaat     660
tgcgtctatg gaggttataa atgctctcgt tgtcctagtt atgccgttca ttcaagatgt     720
gcaacaagaa aagaagtgtg ggatgggtta gagctcgaag atgtgcccga ggaagaagaa     780
gaaatcgaag atcctttcaa ggtaattaat gataagggag atatcattca ttttagtcat     840
gaagagcatg ttctcagatt ggatgagaat tatgttatag atgatgctaa catgcgatgt     900
cggtgttgca ttcttgctat caacggtgat ccatgctaca gatgtgtgga atgtaatttc     960
atccttcacg aagcgtgtgc taaccttcct aggaagaaac gacatttatt gcacaaccat    1020
aaactcactc tttcatcgac acttatcaat aaagatattt ttcatgagtg tggagcttgt    1080
gggatctata cagatggttt catatacgag tgtcgtcatg aagattgcaa aaagaaaatt    1140
attaagtatg atgttcggtg tagttctgta tcagaaccgt ttcaccatga tttgcatcaa    1200
catccctata ctttaccttg caaagttcga gacgatgtca ggcttgtaac aaagaaataa    1260
```

<210> SEQ ID NO 2
<211> LENGTH: 419
<212> TYPE: PRT
<213> ORGANISM: Arabidopsis Thaliana

<400> SEQUENCE: 2

```
Met Ser Ser Thr Asp Asp Phe Glu Val Glu Thr Ile Ser Glu Ile Met
1               5                   10                  15

Val Pro Phe His His His Pro Leu Ser Ser Tyr Ala Ser Glu Phe Leu
            20                  25                  30

Thr Ser Cys Ser Leu Cys Leu Phe Ser Thr Phe Leu Gly Glu Ile Val
        35                  40                  45

Thr Arg Ile Arg Tyr Gln Cys Met Asp Cys Gly Leu Lys Leu His Asp
    50                  55                  60

Glu Cys Ile Asn Ser Leu Ser Leu Asn Arg Pro Phe Leu Cys Asn His
65                  70                  75                  80

Ile Leu Lys Val Tyr Thr His Ile Phe Thr Ser Ser Gly Arg Ile Tyr
                85                  90                  95
```

-continued

Glu Asn Thr Cys His Phe Cys Gln Ser Lys Leu Glu Phe Leu Phe Ala
100 105 110

Arg Cys Thr Ile Cys Asn Leu Asn Val Asp Ile Glu Cys Leu Phe Ala
115 120 125

Leu Pro Pro Leu Thr Ile Ser Glu Pro Lys His His Lys His Ser Leu
130 135 140

Ser Leu Leu Leu Arg Leu Val Thr Phe Thr Cys Asn Ala Cys Gly Val
145 150 155 160

Glu Gly Asp Arg Asn Pro Tyr Val Cys Leu Glu Cys Asn Leu Met Val
165 170 175

His Lys Asp Cys Val Glu Asn Leu Pro Arg Val Ile Ser Ile Asn Arg
180 185 190

His Asp His Arg Ile Ser His Thr Phe His Leu Gly Lys Lys Glu Gly
195 200 205

Asp Trp Glu Cys Gly Val Cys Arg Lys Met Ile Asn Cys Val Tyr Gly
210 215 220

Gly Tyr Lys Cys Ser Arg Cys Pro Ser Tyr Ala Val His Ser Arg Cys
225 230 235 240

Ala Thr Arg Lys Glu Val Trp Asp Gly Leu Glu Leu Glu Asp Val Pro
245 250 255

Glu Glu Glu Glu Glu Ile Glu Asp Pro Phe Lys Val Ile Asn Asp Lys
260 265 270

Gly Asp Ile Ile His Phe Ser His Glu Glu His Val Leu Arg Leu Asp
275 280 285

Glu Asn Tyr Val Ile Asp Asp Ala Asn Met Arg Cys Arg Cys Cys Ile
290 295 300

Leu Ala Ile Asn Gly Asp Pro Cys Tyr Arg Cys Val Glu Cys Asn Phe
305 310 315 320

Ile Leu His Glu Ala Cys Ala Asn Leu Pro Arg Lys Lys Arg His Leu
325 330 335

Leu His Asn His Lys Leu Thr Leu Ser Ser Thr Leu Ile Asn Lys Asp
340 345 350

Ile Phe His Glu Cys Gly Ala Cys Gly Ile Tyr Thr Asp Gly Phe Ile
355 360 365

Tyr Glu Cys Arg His Glu Asp Cys Lys Lys Lys Ile Ile Lys Tyr Asp
370 375 380

Val Arg Cys Ser Ser Val Ser Glu Pro Phe His His Asp Leu His Gln
385 390 395 400

His Pro Tyr Thr Leu Pro Cys Lys Val Arg Asp Asp Val Arg Leu Val
405 410 415

Thr Lys Lys

<210> SEQ ID NO 3
<211> LENGTH: 1107
<212> TYPE: DNA
<213> ORGANISM: Arabidopsis Thaliana

<400> SEQUENCE: 3
atgaaccatc gtgaagaagc aaagagggca aacaatgatg aagacaacgg tggtatagat 60
atagttgtag aaaaatctca tgatttaatt tcaggagggt cggtcccgaa gcttctcaag 120
aaatcagccg gtggagaaaa gtgttgcatc tttagaatcc atcagagact ccggaacaac 180
aactacaagg acgcttacga accaagggtt ctctcaatcg gtccatacca tcatggaaaa 240

-continued

```
gaacatctcc aaatgattca agagcacaaa catcgatttc tcgggatctt catggatgaa    300

gctcaaaaga agggtgtgga tatgaaggat ttgatagaag cagtgtcaga gttggaagaa    360

gatataagag agtcctattc cgagagtctt tataatggtg atgtatctgg tcggaagaaa    420

ttgattgata tgatggttct tgattgttgt ttcattctga ttttgttcct ggtggtagct    480

agaaaagtca gctaccctga gcgtgtgaag gatcctattt tcggaatgaa atggatttta    540

acggctaaag gagtgaccta ctacttttgg agaatcaggg ggataaagtt cgaactgagg    600

aacaatgcaa aaacgctatt ggatataaga cacaaaagaa atcttcttga gattccacca    660

atgatctttg atgaatttct catcttgttc ttctttaatt gtgttgcctt tgaagatttt    720

tatgcttatt gtaccaagca cataacaagc tacgtttttt tcatgggatg tcttctcgaa    780

aacgaggacg atgcgagatt gctttgccgc aaaggaatta taacaaactg tatcggatca    840

gtgaatgaga tctctcaatt ctataaggtc atcggtacag atagccactt ttatctcaac    900

gcgagttact tagctgatgt tttcgaagga gttaatgaat atagttcacg aggatggcat    960

gcatattggt cggtattcaa gaatacccag cttacttacg atactcctcg cacatgtctt   1020

tcatgttgca ctggtttgac gattctcctt ctcacgacat tacaagccgt ctttgcagtg   1080

tatgcctatt atcgtcctcc gaagtga                                        1107
```

<210> SEQ ID NO 4
<211> LENGTH: 368
<212> TYPE: PRT
<213> ORGANISM: Arabidopsis Thaliana

<400> SEQUENCE: 4

```
Met Asn His Arg Glu Glu Ala Lys Arg Ala Asn Asn Asp Glu Asp Asn
1               5                   10                  15

Gly Gly Ile Asp Ile Val Val Glu Lys Ser His Asp Leu Ile Ser Gly
            20                  25                  30

Gly Ser Val Pro Lys Leu Leu Lys Lys Ser Ala Gly Gly Glu Lys Cys
        35                  40                  45

Cys Ile Phe Arg Ile His Gln Arg Leu Arg Asn Asn Asn Tyr Lys Asp
    50                  55                  60

Ala Tyr Glu Pro Arg Val Leu Ser Ile Gly Pro Tyr His His Gly Lys
65                  70                  75                  80

Glu His Leu Gln Met Ile Gln Glu His Lys His Arg Phe Leu Gly Ile
                85                  90                  95

Phe Met Asp Glu Ala Gln Lys Lys Gly Val Asp Met Lys Asp Leu Ile
            100                 105                 110

Glu Ala Val Ser Glu Leu Glu Glu Asp Ile Arg Glu Ser Tyr Ser Glu
        115                 120                 125

Ser Leu Tyr Asn Gly Asp Val Ser Gly Arg Lys Lys Leu Ile Asp Met
    130                 135                 140

Met Val Leu Asp Cys Cys Phe Ile Leu Ile Leu Phe Leu Val Val Ala
145                 150                 155                 160

Arg Lys Val Ser Tyr Pro Glu Arg Val Lys Asp Pro Ile Phe Gly Met
                165                 170                 175

Lys Trp Ile Leu Thr Ala Lys Gly Val Thr Tyr Tyr Phe Trp Arg Ile
            180                 185                 190

Arg Gly Ile Lys Phe Glu Leu Arg Asn Asn Ala Lys Thr Leu Leu Asp
        195                 200                 205

Ile Arg His Lys Arg Asn Leu Leu Glu Ile Pro Pro Met Ile Phe Asp
    210                 215                 220
```

```
Glu Phe Leu Ile Leu Phe Phe Phe Asn Cys Val Ala Phe Glu Asp Phe
225                 230                 235                 240

Tyr Ala Tyr Cys Thr Lys His Ile Thr Ser Tyr Val Phe Phe Met Gly
                245                 250                 255

Cys Leu Leu Glu Asn Glu Asp Asp Ala Arg Leu Leu Cys Arg Lys Gly
            260                 265                 270

Ile Ile Thr Asn Cys Ile Gly Ser Val Asn Glu Ile Ser Gln Phe Tyr
        275                 280                 285

Lys Val Ile Gly Thr Asp Ser His Phe Tyr Leu Asn Ala Ser Tyr Leu
    290                 295                 300

Ala Asp Val Phe Glu Gly Val Asn Glu Tyr Ser Ser Arg Gly Trp His
305                 310                 315                 320

Ala Tyr Trp Ser Val Phe Lys Asn Thr Gln Leu Thr Tyr Asp Thr Pro
                325                 330                 335

Arg Thr Cys Leu Ser Cys Cys Thr Gly Leu Thr Ile Leu Leu Leu Thr
            340                 345                 350

Thr Leu Gln Ala Val Phe Ala Val Tyr Ala Tyr Tyr Arg Pro Pro Lys
        355                 360                 365


<210> SEQ ID NO 5
<211> LENGTH: 270
<212> TYPE: DNA
<213> ORGANISM: Arabidopsis Thaliana

<400> SEQUENCE: 5

atggcggatt ggggacctgt tgtagtcgct gtgatactgt tcgtgctttt gactccggga      60

cttctctttc agattccggc gagaggtcgt gttgttgaat ttggtaatat gcagactagt     120

ggagcgtcga ttctcgtcca caccatcatt ttcttcggtc ttataaccat cttcaccatc     180

gccattcgtc tccatatcta taccggcact aggcagttag ccttagtttg gtttattggt     240

attcgagttc aaattggaat tgagtactaa                                      270


<210> SEQ ID NO 6
<211> LENGTH: 89
<212> TYPE: PRT
<213> ORGANISM: Arabidopsis Thaliana

<400> SEQUENCE: 6

Met Ala Asp Trp Gly Pro Val Val Val Ala Val Ile Leu Phe Val Leu
1               5                   10                  15

Leu Thr Pro Gly Leu Leu Phe Gln Ile Pro Ala Arg Gly Arg Val Val
            20                  25                  30

Glu Phe Gly Asn Met Gln Thr Ser Gly Ala Ser Ile Leu Val His Thr
        35                  40                  45

Ile Ile Phe Phe Gly Leu Ile Thr Ile Phe Thr Ile Ala Ile Arg Leu
    50                  55                  60

His Ile Tyr Thr Gly Thr Arg Gln Leu Ala Leu Val Trp Phe Ile Gly
65                  70                  75                  80

Ile Arg Val Gln Ile Gly Ile Glu Tyr
                85


<210> SEQ ID NO 7
<211> LENGTH: 1146
<212> TYPE: DNA
<213> ORGANISM: Arabidopsis Thaliana

<400> SEQUENCE: 7
```

```
cacattattc gagagaaatg gaatcagcca atcactctct ttcctccata tataaaatct      60

agccaatatt cacaaataat aactacttcc ttcgttcttt tccttaccaa aagatccacc     120

tcgaacctct ctcctccgtc ttcctccgca gccgccgtca ctatcaccgc agctagaatg     180

agagaagata atccaaattg gttccttaga tgggaagaag agcttccatc tccagaagaa     240

ctcatcccta tctctcaaac cttaatcact cctcatctag ctctcgcttt ccaaatcgga     300

agtcctaatc atcatctcgg atcaaagaga accaccgcga tttatcacca gaagcttcaa     360

tcctccacca ctccaacaac tccaactcca actcctccac cgatgatgat gaattctgat     420

ttcggcggtg gcgattccac ggatcttggt tcaggatcaa taggaggaga gccagcaaga     480

acgttgaaac ggccgcgtct agtgtggacg cctcagctac acaaacgttt cgtggatgcg     540

gttggacact tagggatcaa aaacgcagtt ccaaagacta taatgcagct tatgagcgtt     600

gaaggattga ctagagagaa cgttgcgagt catcttcaga aatatcgtct ttaccttagg     660

agaatgcaag gcgggaacgg taacggaatc actggaggac acgtcatcgt ctctgattcg     720

gctactgatc ggctatttgc tagctcaccg gttccagctc atttcttgag cccggattac     780

ttgatgccgc cattagagca ttcgtatatg ggaaacatg tgattacgca gcaaaaccaa      840

gtggttcgta atctgaggta tgaagattcg gaatatggtc atggtagtat gaagatgctt     900

aagctcttcc ctgccggaaa ttaatgaaat atttgaattc ttaacttcat ttttatggaa     960

gtaataatgt ttaaggtatg tggattatct ctgtaatttg catttgtcgt caggatcaat    1020

aatctattgt tagtgtatat tatttgttac gcgaacaatt taacctttgt atgatgttat    1080

catttgaatt cactacaaca cagtagcttg tttttatttc tttcgtctat tcattagttt    1140

ccctgg                                                               1146
```

<210> SEQ ID NO 8
<211> LENGTH: 248
<212> TYPE: PRT
<213> ORGANISM: Arabidopsis Thaliana

<400> SEQUENCE: 8

```
Met Arg Glu Asp Asn Pro Asn Trp Phe Leu Arg Trp Glu Glu Glu Leu
1               5                   10                  15

Pro Ser Pro Glu Glu Leu Ile Pro Ile Ser Gln Thr Leu Ile Thr Pro
            20                  25                  30

His Leu Ala Leu Ala Phe Gln Ile Gly Ser Pro Asn His His Leu Gly
        35                  40                  45

Ser Lys Arg Thr Thr Ala Ile Tyr His Gln Lys Leu Gln Ser Ser Thr
    50                  55                  60

Thr Pro Thr Thr Pro Thr Pro Thr Pro Pro Pro Met Met Met Asn Ser
65                  70                  75                  80

Asp Phe Gly Gly Gly Asp Ser Thr Asp Leu Gly Ser Gly Ser Ile Gly
                85                  90                  95

Gly Glu Pro Ala Arg Thr Leu Lys Arg Pro Arg Leu Val Trp Thr Pro
            100                 105                 110

Gln Leu His Lys Arg Phe Val Asp Ala Val Gly His Leu Gly Ile Lys
        115                 120                 125

Asn Ala Val Pro Lys Thr Ile Met Gln Leu Met Ser Val Glu Gly Leu
    130                 135                 140

Thr Arg Glu Asn Val Ala Ser His Leu Gln Lys Tyr Arg Leu Tyr Leu
145                 150                 155                 160
```

-continued

```
Arg Arg Met Gln Gly Gly Asn Gly Asn Gly Ile Thr Gly Gly His Val
                165                 170                 175

Ile Val Ser Asp Ser Ala Thr Asp Arg Leu Phe Ala Ser Ser Pro Val
            180                 185                 190

Pro Ala His Phe Leu Ser Pro Asp Tyr Leu Met Pro Pro Leu Glu His
        195                 200                 205

Ser Tyr Met Gly Lys His Val Ile Thr Gln Gln Asn Gln Val Val Arg
    210                 215                 220

Asn Leu Arg Tyr Glu Asp Ser Glu Tyr Gly His Gly Ser Met Lys Met
225                 230                 235                 240

Leu Lys Leu Phe Pro Ala Gly Asn
                245
```

<210> SEQ ID NO 9
<211> LENGTH: 1811
<212> TYPE: DNA
<213> ORGANISM: Arabidopsis Thaliana

<400> SEQUENCE: 9

```
gtttttcac aaccaaattt ccattataaa tcaaaaaata aaaacttaat tagtttttac      60

agaagaaaag aaaacaatga gaggtaaatt tctaagttta ctgttgctca ttactttggc     120

ctgcattgga gtttccgcca agaagcattc cacaaggcct agattaagaa gaaatgattt     180

cccacaagat ttcgtttttg gatctgctac ttctgcttat cagtgtgaag gagctgcaca     240

tgaagatggt agaggtccaa gtatctggga ctccttctct gaaaaattcc cagaaaagat     300

aatggatggt agtaatgggt ccattgcaga tgattcttac aatctttaca aggaagatgt     360

gaatttgctg catcaaattg gcttcgatgc ttaccgattt tcgatctcat ggtcacggat     420

tttgcctcgt gggactctaa agggaggaat caaccaggct ggaattgaat attataacaa     480

cttgattaat caacttatat ctaaaggagt gaagccattt gtcacactct ttcactggga     540

cttaccagat gcactcgaaa atgcttacgg tggcctcctt ggagatgaat ttgtgaacga     600

tttccgagac tatgcagaac tttgtttcca gaagtttgga gatagagtga agcagtggac     660

gacactaaac gagccatata caatggtaca tgaaggttat ataacaggtc aaaaggcacc     720

tggaagatgt tccaatttct ataaacctga ttgcttaggt ggcgatgcag ccacggagcc     780

ttacatcgtc ggccataacc tcctccttgc tcatggagtt gccgtaaaag tatatagaga     840

aaagtaccag gcaactcaga aaggtgaaat tggtattgcc ttaaacacag catggcacta     900

cccttattca gattcatatg ctgaccggtt agctgcgact cgagcgactg ccttcacctt     960

cgactacttc atggagccaa tcgtgtacgg tagatatcca attgaaatgg tcagccacgt    1020

taaagacggt cgtcttccta ccttcacacc agaagagtcc gaaatgctca aggatcata     1080

tgatttcata ggcgttaact attactcatc tctttacgca aaagacgtgc cgtgtgcaac    1140

tgaaaacatc accatgacca ccgattcttg cgtcagcctc gtaggtgaac gaaatggagt    1200

gcctatcggt ccagcggctg gatcggattg gcttttgata tatcccaagg gtattcgtga    1260

tctcctacta catgcaaaat tcagatacaa tgatcccgtc ttgtacatta cagagaatgg    1320

agtggatgaa gcaaatattg gcaaaatatt tcttaacgac gatttgagaa ttgattacta    1380

tgctcatcac ctcaagatgg ttagcgatgc tatctcgatc ggggtgaatg tgaagggata    1440

tttcgcgtgg tcattgatgg ataatttcga gtggtcggaa ggatacacgg tccggttcgg    1500

gctagtgttt gtggactttg aagatggacg taagaggtat ctgaagaaat cagctaagtg    1560

gtttaggaga ttgttgaagg gagcgcatgg tgggacgaat gagcaggtgg ctgttattta    1620
```

```
ataaaccacg agtcattggt caatttagtc tactgtttct tttgctctat gtacagaaag   1680

aaaataaact ttccaaaata agaggtggct ttgtttggac tttggatgtt actatatata   1740

ttggtaattc ttggcgtttg ttagtttcca aaccaaacat taataaataa ataaataaaa   1800

gagttgaggt t                                                        1811


<210> SEQ ID NO 10
<211> LENGTH: 514
<212> TYPE: PRT
<213> ORGANISM: Arabidopsis Thaliana

<400> SEQUENCE: 10

Met Arg Gly Lys Phe Leu Ser Leu Leu Leu Leu Ile Thr Leu Ala Cys
1               5                   10                  15

Ile Gly Val Ser Ala Lys Lys His Ser Thr Arg Pro Arg Leu Arg Arg
            20                  25                  30

Asn Asp Phe Pro Gln Asp Phe Val Phe Gly Ser Ala Thr Ser Ala Tyr
        35                  40                  45

Gln Cys Glu Gly Ala Ala His Glu Asp Gly Arg Gly Pro Ser Ile Trp
    50                  55                  60

Asp Ser Phe Ser Glu Lys Phe Pro Glu Lys Ile Met Asp Gly Ser Asn
65                  70                  75                  80

Gly Ser Ile Ala Asp Asp Ser Tyr Asn Leu Tyr Lys Glu Asp Val Asn
                85                  90                  95

Leu Leu His Gln Ile Gly Phe Asp Ala Tyr Arg Phe Ser Ile Ser Trp
            100                 105                 110

Ser Arg Ile Leu Pro Arg Gly Thr Leu Lys Gly Gly Ile Asn Gln Ala
        115                 120                 125

Gly Ile Glu Tyr Tyr Asn Asn Leu Ile Asn Gln Leu Ile Ser Lys Gly
    130                 135                 140

Val Lys Pro Phe Val Thr Leu Phe His Trp Asp Leu Pro Asp Ala Leu
145                 150                 155                 160

Glu Asn Ala Tyr Gly Gly Leu Leu Gly Asp Glu Phe Val Asn Asp Phe
                165                 170                 175

Arg Asp Tyr Ala Glu Leu Cys Phe Gln Lys Phe Gly Asp Arg Val Lys
            180                 185                 190

Gln Trp Thr Thr Leu Asn Glu Pro Tyr Thr Met Val His Glu Gly Tyr
        195                 200                 205

Ile Thr Gly Gln Lys Ala Pro Gly Arg Cys Ser Asn Phe Tyr Lys Pro
    210                 215                 220

Asp Cys Leu Gly Gly Asp Ala Ala Thr Glu Pro Tyr Ile Val Gly His
225                 230                 235                 240

Asn Leu Leu Leu Ala His Gly Val Ala Val Lys Val Tyr Arg Glu Lys
                245                 250                 255

Tyr Gln Ala Thr Gln Lys Gly Glu Ile Gly Ile Ala Leu Asn Thr Ala
            260                 265                 270

Trp His Tyr Pro Tyr Ser Asp Ser Tyr Ala Asp Arg Leu Ala Ala Thr
        275                 280                 285

Arg Ala Thr Ala Phe Thr Phe Asp Tyr Phe Met Glu Pro Ile Val Tyr
    290                 295                 300

Gly Arg Tyr Pro Ile Glu Met Val Ser His Val Lys Asp Gly Arg Leu
305                 310                 315                 320

Pro Thr Phe Thr Pro Glu Glu Ser Glu Met Leu Lys Gly Ser Tyr Asp
                325                 330                 335
```

-continued

```
Phe Ile Gly Val Asn Tyr Tyr Ser Ser Leu Tyr Ala Lys Asp Val Pro
            340                 345                 350

Cys Ala Thr Glu Asn Ile Thr Met Thr Thr Asp Ser Cys Val Ser Leu
        355                 360                 365

Val Gly Glu Arg Asn Gly Val Pro Ile Gly Pro Ala Ala Gly Ser Asp
    370                 375                 380

Trp Leu Leu Ile Tyr Pro Lys Gly Ile Arg Asp Leu Leu Leu His Ala
385                 390                 395                 400

Lys Phe Arg Tyr Asn Asp Pro Val Leu Tyr Ile Thr Glu Asn Gly Val
                405                 410                 415

Asp Glu Ala Asn Ile Gly Lys Ile Phe Leu Asn Asp Asp Leu Arg Ile
            420                 425                 430

Asp Tyr Tyr Ala His His Leu Lys Met Val Ser Asp Ala Ile Ser Ile
        435                 440                 445

Gly Val Asn Val Lys Gly Tyr Phe Ala Trp Ser Leu Met Asp Asn Phe
    450                 455                 460

Glu Trp Ser Glu Gly Tyr Thr Val Arg Phe Gly Leu Val Phe Val Asp
465                 470                 475                 480

Phe Glu Asp Gly Arg Lys Arg Tyr Leu Lys Lys Ser Ala Lys Trp Phe
                485                 490                 495

Arg Arg Leu Leu Lys Gly Ala His Gly Gly Thr Asn Glu Gln Val Ala
            500                 505                 510

Val Ile


<210> SEQ ID NO 11
<211> LENGTH: 1605
<212> TYPE: DNA
<213> ORGANISM: Arabidopsis Thaliana

<400> SEQUENCE: 11

atgtactcga agaaaaactc gttcggccga tcagatttcc cagagggttt ccttttcggt      60

acagcttcat cggcttacca atatgaagga gccagaaacg aagctcctcg aggagagagt     120

gtttgggaca catttgttcg caaatatcca gagagaaatt gctactctaa tgcggaccaa     180

gcaatcgagt tctataacca ttacaaggac gatatccaga gaatgaagga tattaacatg     240

gatgctttca gattctctat ctcttggcct aggatttttc ctcttggaaa gaaaagcaaa     300

ggagtgaaca aagaaggaat acaattctat aacgatctca tcgatgaact cctcgctaac     360

ggaataacac ctctcgccac tttatttcac tgggatactc ctcaagcact tgaagatgaa     420

tacagtggat ttttaagcga agaagctgtt gatgacttca aggattttgc ggccttatgt     480

tttgaggagt ttggcgaccg tgtaaaattg tgggtcacac taaacgaacc atgggtgtac     540

agtattggtg gctatgacac gggaagaaaa gcccccggac gtgcctccaa atacatgaac     600

gaagcagccg tggcaggaga atctggtctc gaggtttaca ctgttagtca caatctactt     660

ctggctcacg ccgaagctgt tgaggtcttc aggaacaatc ccaaatgtaa agatggcaag     720

atcggtatcg ctcattgtcc cgtatggttc gagccttatg actcgaactg ccctaaagac     780

atagaagcat gcgaacgagc tatggagttt atgtttggat ggcacatgga tcctacggtg     840

tatggagatt accctgcagt catgaaaaaa tcgatcggaa aaagattacc atcatttacc     900

gcagcacaat ccaagaagct tagaggatct tttgatttcg ttggggtgaa ttattacagt     960

gctttctacg tcaaaaatat tgatgaagtg aatcatgaca agcccaattg gagatcagac    1020

gcacgcatcg aatggagaaa agaaaacaac gcagggcaaa cattaggtgt aagaggtggt    1080
```

```
tcggaatggg actttctata tccacaaggc cttagaaagt ttctaaatta tgccaagaat   1140

aaatatgaaa gcccgaaatt tatgattacc gaaaacggac actgtgatat agattatgag   1200

aaaaagccta aactttctaa cttgatggat ctccaaagga cagagtacca caagaaacat   1260

ctccaaagca tccaacaagc catccaggag gatggggttg tagttgaagg atactttgcg   1320

tggtcattac tagacaattg tgaatggaac gccggttatg gagttcgata tggactattc   1380

tacgtcgatt ataacaatgg actaaaacgt ttcccgaaaa tgtcggcgat gtggttcaaa   1440

gaattcttga agagagaaga agaaattgaa gattcagaag aagaagagta cgtgttgaag   1500

tcaacaatga acaagaagag attcttatta gcaactggtt catcagcttc atgctttatt   1560

cctaagatgt ctgaatcttc taaagccctc gaactattat tctag                    1605


<210> SEQ ID NO 12
<211> LENGTH: 534
<212> TYPE: PRT
<213> ORGANISM: Arabidopsis Thaliana

<400> SEQUENCE: 12

Met Tyr Ser Lys Lys Asn Ser Phe Gly Arg Ser Asp Phe Pro Glu Gly
1               5                   10                  15

Phe Leu Phe Gly Thr Ala Ser Ser Ala Tyr Gln Tyr Glu Gly Ala Arg
            20                  25                  30

Asn Glu Ala Pro Arg Gly Glu Ser Val Trp Asp Thr Phe Val Arg Lys
        35                  40                  45

Tyr Pro Glu Arg Asn Cys Tyr Ser Asn Ala Asp Gln Ala Ile Glu Phe
    50                  55                  60

Tyr Asn His Tyr Lys Asp Asp Ile Gln Arg Met Lys Asp Ile Asn Met
65                  70                  75                  80

Asp Ala Phe Arg Phe Ser Ile Ser Trp Pro Arg Ile Phe Pro Leu Gly
                85                  90                  95

Lys Lys Ser Lys Gly Val Asn Lys Glu Gly Ile Gln Phe Tyr Asn Asp
            100                 105                 110

Leu Ile Asp Glu Leu Leu Ala Asn Gly Ile Thr Pro Leu Ala Thr Leu
        115                 120                 125

Phe His Trp Asp Thr Pro Gln Ala Leu Glu Asp Glu Tyr Ser Gly Phe
    130                 135                 140

Leu Ser Glu Glu Ala Val Asp Asp Phe Lys Asp Phe Ala Ala Leu Cys
145                 150                 155                 160

Phe Glu Glu Phe Gly Asp Arg Val Lys Leu Trp Val Thr Leu Asn Glu
                165                 170                 175

Pro Trp Val Tyr Ser Ile Gly Gly Tyr Asp Thr Gly Arg Lys Ala Pro
            180                 185                 190

Gly Arg Ala Ser Lys Tyr Met Asn Glu Ala Ala Val Ala Gly Glu Ser
        195                 200                 205

Gly Leu Glu Val Tyr Thr Val Ser His Asn Leu Leu Leu Ala His Ala
    210                 215                 220

Glu Ala Val Glu Val Phe Arg Asn Asn Pro Lys Cys Lys Asp Gly Lys
225                 230                 235                 240

Ile Gly Ile Ala His Cys Pro Val Trp Phe Glu Pro Tyr Asp Ser Asn
                245                 250                 255

Cys Pro Lys Asp Ile Glu Ala Cys Glu Arg Ala Met Glu Phe Met Phe
            260                 265                 270

Gly Trp His Met Asp Pro Thr Val Tyr Gly Asp Tyr Pro Ala Val Met
```

-continued

```
        275                 280                 285

Lys Lys Ser Ile Gly Lys Arg Leu Pro Ser Phe Thr Ala Ala Gln Ser
    290                 295                 300

Lys Lys Leu Arg Gly Ser Phe Asp Phe Val Gly Val Asn Tyr Tyr Ser
305                 310                 315                 320

Ala Phe Tyr Val Lys Asn Ile Asp Glu Val Asn His Asp Lys Pro Asn
                325                 330                 335

Trp Arg Ser Asp Ala Arg Ile Glu Trp Arg Lys Glu Asn Asn Ala Gly
            340                 345                 350

Gln Thr Leu Gly Val Arg Gly Gly Ser Glu Trp Asp Phe Leu Tyr Pro
        355                 360                 365

Gln Gly Leu Arg Lys Phe Leu Asn Tyr Ala Lys Asn Lys Tyr Glu Ser
    370                 375                 380

Pro Lys Phe Met Ile Thr Glu Asn Gly His Cys Asp Ile Asp Tyr Glu
385                 390                 395                 400

Lys Lys Pro Lys Leu Ser Asn Leu Met Asp Leu Gln Arg Thr Glu Tyr
                405                 410                 415

His Lys Lys His Leu Gln Ser Ile Gln Gln Ala Ile Gln Glu Asp Gly
            420                 425                 430

Val Val Val Glu Gly Tyr Phe Ala Trp Ser Leu Leu Asp Asn Cys Glu
        435                 440                 445

Trp Asn Ala Gly Tyr Gly Val Arg Tyr Gly Leu Phe Tyr Val Asp Tyr
    450                 455                 460

Asn Asn Gly Leu Lys Arg Phe Pro Lys Met Ser Ala Met Trp Phe Lys
465                 470                 475                 480

Glu Phe Leu Lys Arg Glu Glu Glu Ile Glu Asp Ser Glu Glu Glu Glu
                485                 490                 495

Tyr Val Leu Lys Ser Thr Met Asn Lys Lys Arg Phe Leu Leu Ala Thr
            500                 505                 510

Gly Ser Ser Ala Ser Cys Phe Ile Pro Lys Met Ser Glu Ser Ser Lys
        515                 520                 525

Ala Leu Glu Leu Leu Phe
    530


<210> SEQ ID NO 13
<211> LENGTH: 1953
<212> TYPE: DNA
<213> ORGANISM: Arabidopsis Thaliana

<400> SEQUENCE: 13

gaccacaaga gccatttgca attaggcata atatatgtcc taactcacca accccctcaa      60

aattgccacc aacttcaaat ttctctcctt taaacctttc tcaatcatct ttcttctgcc     120

ttggaatcct gatcatggcg tcgtcttctc tcacttcgaa atccattctc ggatccacca     180

aactcggttc ttcttctctt ccctcggagc tccgtcgtct ctcttctccc gccgttcaga     240

tctctctccg tacccaaacc aggaagaact tccagataca agctactgga agttcatatg     300

ggactcattt tcgagtttca acttttggag aatcacatgg aggaggagtt ggttgtatca     360

ttgatggttg tcctcctcgt attccactta ctgaatctga tttgcaattc gatctcgata     420

gaaggaggcc tggtcagagc aggatcacaa ctcctagaaa agagactgat acttgccgga     480

tatcgtctgg agtctctgaa ggaatgacga caggaacacc tatccatgtg tttgtaccaa     540

acacagatca gagaggactt gattacagtg aaatgtcggt tgcctataga ccatcgcatg     600

ctgatgcaac ttatgacatg aagtatggtg tcagatcagt gcagggtgga ggaagatctt     660
```

-continued

```
cagctagaga gaccattgga agagttgctc ctggagcttt ggccaagaaa attttgaagc    720

aatttgcagg aactgagatt cttgcctatg tctcgcaagt tcaccatgtt gtacttccag    780

aagaattggt agaccacgag aatttaacac tcgaacagat agaaaataac attgtcagat    840

gccctaatcc cgagtatgcg gaaaagatga tagctgcgat tgatgctgtc aggacaaaag    900

ggaactctgt tggtggtgtt gtgacctgca ttgttcggaa tgctccacgt gggcttggta    960

caccggtttt cgataaactt gaagcagaac tggcaaaagc ttgtatgtcg ctacctgcaa   1020

ctaagggatt tgagtttgga agcggctttg caggtacctt tttgactggt cttgaacaca   1080

atgatgagtt ctataccgat gaaaatggaa gaatacgtac cagaaccaac cgatctggtg   1140

gaattcaggg agggatctca aatggtgaaa taataaacat gagagtagcc ttcaagccaa   1200

catcaacaat tggaaggaag caaaatacgg taaccagaga caaggtagaa accgaaatga   1260

ttgcgcgtgg tcgtcatgat ccttgtgttg ttccacgagc tgtgccaatg gtggaagcaa   1320

tggtggctct agttcttgtg gatcaattga tggcgcaata cgcacaatgc catttgtttc   1380

caataaatcc agagttgcag gaacctctcc agatagagca gccgcaaaat gctactgctt   1440

tgtaagcaaa tctcgagaag ataaagagtc atagagagtg agagttcgct tttgttgtgt   1500

gattattatg ctgaataaaa aaatgttaat tttgtgccca ccagaaaaac aaagaacatg   1560

attttttata agaggatttg cttctatatc attcagctaa atgtgatttt accacgaaca   1620

taaactattt tctataattt ttttggtgta aaaccaaaca cttttctaca acatacatga   1680

tacatgtaaa tatacaaaca aacgtaacta attacacatt gctctgttct ctgttttttt   1740

tcgtactctc gtgggacgaa aaccgacgta gtttttttca gatgttttta cttggttttc   1800

ttgttatcgt ctttgctctg ttcaagaagg accggagcag ccggaatgct aaaccaccac   1860

tctttaagcc gccgcatcaa ccgttccgtg cttgctcttc gtggtggtga gtatcttgtg   1920

aacagttcaa gaaacaccac cagaatcaga ttg                                1953
```

<210> SEQ ID NO 14
<211> LENGTH: 436
<212> TYPE: PRT
<213> ORGANISM: Arabidopsis Thaliana

<400> SEQUENCE: 14

```
Met Ala Ser Ser Ser Leu Thr Ser Lys Ser Ile Leu Gly Ser Thr Lys
1               5                   10                  15

Leu Gly Ser Ser Ser Leu Pro Ser Glu Leu Arg Arg Leu Ser Ser Pro
            20                  25                  30

Ala Val Gln Ile Ser Leu Arg Thr Gln Thr Arg Lys Asn Phe Gln Ile
        35                  40                  45

Gln Ala Thr Gly Ser Ser Tyr Gly Thr His Phe Arg Val Ser Thr Phe
    50                  55                  60

Gly Glu Ser His Gly Gly Gly Val Gly Cys Ile Ile Asp Gly Cys Pro
65                  70                  75                  80

Pro Arg Ile Pro Leu Thr Glu Ser Asp Leu Gln Phe Asp Leu Asp Arg
                85                  90                  95

Arg Arg Pro Gly Gln Ser Arg Ile Thr Thr Pro Arg Lys Glu Thr Asp
            100                 105                 110

Thr Cys Arg Ile Ser Ser Gly Val Ser Glu Gly Met Thr Thr Gly Thr
        115                 120                 125

Pro Ile His Val Phe Val Pro Asn Thr Asp Gln Arg Gly Leu Asp Tyr
    130                 135                 140
```

```
Ser Glu Met Ser Val Ala Tyr Arg Pro Ser His Ala Asp Ala Thr Tyr
145                 150                 155                 160

Asp Met Lys Tyr Gly Val Arg Ser Val Gln Gly Gly Gly Arg Ser Ser
                165                 170                 175

Ala Arg Glu Thr Ile Gly Arg Val Ala Pro Gly Ala Leu Ala Lys Lys
            180                 185                 190

Ile Leu Lys Gln Phe Ala Gly Thr Glu Ile Leu Ala Tyr Val Ser Gln
        195                 200                 205

Val His His Val Val Leu Pro Glu Glu Leu Val Asp His Glu Asn Leu
    210                 215                 220

Thr Leu Glu Gln Ile Glu Asn Asn Ile Val Arg Cys Pro Asn Pro Glu
225                 230                 235                 240

Tyr Ala Glu Lys Met Ile Ala Ala Ile Asp Ala Val Arg Thr Lys Gly
                245                 250                 255

Asn Ser Val Gly Gly Val Val Thr Cys Ile Val Arg Asn Ala Pro Arg
            260                 265                 270

Gly Leu Gly Thr Pro Val Phe Asp Lys Leu Glu Ala Glu Leu Ala Lys
        275                 280                 285

Ala Cys Met Ser Leu Pro Ala Thr Lys Gly Phe Glu Phe Gly Ser Gly
    290                 295                 300

Phe Ala Gly Thr Phe Leu Thr Gly Leu Glu His Asn Asp Glu Phe Tyr
305                 310                 315                 320

Thr Asp Glu Asn Gly Arg Ile Arg Thr Arg Thr Asn Arg Ser Gly Gly
                325                 330                 335

Ile Gln Gly Gly Ile Ser Asn Gly Glu Ile Ile Asn Met Arg Val Ala
            340                 345                 350

Phe Lys Pro Thr Ser Thr Ile Gly Arg Lys Gln Asn Thr Val Thr Arg
        355                 360                 365

Asp Lys Val Glu Thr Glu Met Ile Ala Arg Gly Arg His Asp Pro Cys
    370                 375                 380

Val Val Pro Arg Ala Val Pro Met Val Glu Ala Met Val Ala Leu Val
385                 390                 395                 400

Leu Val Asp Gln Leu Met Ala Gln Tyr Ala Gln Cys His Leu Phe Pro
                405                 410                 415

Ile Asn Pro Glu Leu Gln Glu Pro Leu Gln Ile Glu Gln Pro Gln Asn
            420                 425                 430

Ala Thr Ala Leu
        435
```

<210> SEQ ID NO 15
<211> LENGTH: 1634
<212> TYPE: DNA
<213> ORGANISM: Arabidopsis Thaliana

<400> SEQUENCE: 15

```
acccaaaaac aaaatctaat agagaaaaat aagtagatat ggcaaccctt aagtgcattg     60

attggcaatt cagcggaagc gaggcggcca aagatgctgc tgcggcctcc ttaggctcat    120

atacctctgc actctatgcc ctgtgcgatc ctcatggcaa acccattttg cccccacgaa    180

atgagatcct ggagaccagc aatacagccg aaaaagcagt tgttaaagct gttctttatg    240

gctcgggaaa cgcctatgct cctagcttag gcctcgcggc cgccaaaagt gccgtagcag    300

agtatctaaa ccaaggtctt ccaaagaagc ttaccgcaga tgacgtgttt atgactctgg    360

gatgcaaaca agctattgag ctcgcggtag acattctcgc taaaccgaaa gccaacgttt    420
```

-continued

```
tgcttccgag tcccggcttc ccatgggacc tagtccgctc catctacaag aaccttgagg    480

tccgccacta taatttcctt ccagaaaaga actttgaaat cgactttgat agcgtccgag    540

cgctcgtgga cgagaacaca tttgccatat ttataatcaa cccccacaac cccaatggta    600

acacctactc cgaggctcat ctcaaacagc tggctgaact ggctaaggaa ctcaagatta    660

tggtggtttc tgacgaggtt tttagatgga cactctttgg tagtaaccct tttgttccta    720

tgggaaaatt ctcgtcgatc gtaccagtgg ttacactcgg atccatatca aagggatgga    780

aagtcccagg atggcgaact ggttggctca cgctacatga tctagacggt gtcttcagaa    840

acaccaaggt cttacaagct gctcaagatt ttctccagat aaacaataac cctccgacag    900

ttatccaggc ggctattcct gacatcttgg agaaaactcc tcaagagttt tttgataaga    960

ggcagagttt tctgaaagat aaagtagaat ttggttattc taagctcaag tacattccta   1020

gcctcacttg ctacatgaaa cccgaagcct gcaccttctt atggaccgag cttgatttat   1080

cgagctttgt ggacatcgaa gacgatcaag actttttgcaa taagcttgct aaagaagaaa   1140

acctcgtcgt tttaccaggg attgcattca gtcagaagaa ctggttgagg cattctatcg   1200

atatggagac tccggtattg gaggatgcat tggaaagatt gaagagcttc tgcgatcgcc   1260

attccaacaa aaaagctccc ctcaaagacg tcaatggtgt taagtaaagg gtcaatatgg   1320

ttatttgcct aagtcattta cgtatgctat aatgataaat aaatgagtgt ttcttggttt   1380

gaggtaaatc atgaacactt tagtgtattt gtaacaaata aaatgggtgc acttaatatc   1440

aatcgtgtgt aatgtttct catagtttgc tatatctttg tgtatatcta tctacttttc   1500

ggaaataaaa tagattgtct gcatttacca ttggaataca tatacatata tacatctctt   1560

aactacttca aaatactttg gacttgtcgt gtcgtgtatt tttagaaaaa ttatgaagaa   1620

acccagtttt acct                                                     1634
```

```
<210> SEQ ID NO 16
<211> LENGTH: 422
<212> TYPE: PRT
<213> ORGANISM: Arabidopsis Thaliana

<400> SEQUENCE: 16

Met Ala Thr Leu Lys Cys Ile Asp Trp Gln Phe Ser Gly Ser Glu Ala
1               5                   10                  15

Ala Lys Asp Ala Ala Ala Ala Ser Leu Gly Ser Tyr Thr Ser Ala Leu
            20                  25                  30

Tyr Ala Leu Cys Asp Pro His Gly Lys Pro Ile Leu Pro Pro Arg Asn
        35                  40                  45

Glu Ile Leu Glu Thr Ser Asn Thr Ala Glu Lys Ala Val Val Lys Ala
    50                  55                  60

Val Leu Tyr Gly Ser Gly Asn Ala Tyr Ala Pro Ser Leu Gly Leu Ala
65                  70                  75                  80

Ala Ala Lys Ser Ala Val Ala Glu Tyr Leu Asn Gln Gly Leu Pro Lys
                85                  90                  95

Lys Leu Thr Ala Asp Asp Val Phe Met Thr Leu Gly Cys Lys Gln Ala
            100                 105                 110

Ile Glu Leu Ala Val Asp Ile Leu Ala Lys Pro Lys Ala Asn Val Leu
        115                 120                 125

Leu Pro Ser Pro Gly Phe Pro Trp Asp Leu Val Arg Ser Ile Tyr Lys
    130                 135                 140

Asn Leu Glu Val Arg His Tyr Asn Phe Leu Pro Glu Lys Asn Phe Glu
```

```
145                 150                 155                 160

Ile Asp Phe Asp Ser Val Arg Ala Leu Val Asp Glu Asn Thr Phe Ala
                165                 170                 175

Ile Phe Ile Ile Asn Pro His Asn Pro Asn Gly Asn Thr Tyr Ser Glu
            180                 185                 190

Ala His Leu Lys Gln Leu Ala Glu Leu Ala Lys Glu Leu Lys Ile Met
        195                 200                 205

Val Val Ser Asp Glu Val Phe Arg Trp Thr Leu Phe Gly Ser Asn Pro
    210                 215                 220

Phe Val Pro Met Gly Lys Phe Ser Ser Ile Val Pro Val Val Thr Leu
225                 230                 235                 240

Gly Ser Ile Ser Lys Gly Trp Lys Val Pro Gly Trp Arg Thr Gly Trp
                245                 250                 255

Leu Thr Leu His Asp Leu Asp Gly Val Phe Arg Asn Thr Lys Val Leu
            260                 265                 270

Gln Ala Ala Gln Asp Phe Leu Gln Ile Asn Asn Asn Pro Pro Thr Val
        275                 280                 285

Ile Gln Ala Ala Ile Pro Asp Ile Leu Glu Lys Thr Pro Gln Glu Phe
    290                 295                 300

Phe Asp Lys Arg Gln Ser Phe Leu Lys Asp Lys Val Glu Phe Gly Tyr
305                 310                 315                 320

Ser Lys Leu Lys Tyr Ile Pro Ser Leu Thr Cys Tyr Met Lys Pro Glu
                325                 330                 335

Ala Cys Thr Phe Leu Trp Thr Glu Leu Asp Leu Ser Ser Phe Val Asp
            340                 345                 350

Ile Glu Asp Asp Gln Asp Phe Cys Asn Lys Leu Ala Lys Glu Glu Asn
        355                 360                 365

Leu Val Val Leu Pro Gly Ile Ala Phe Ser Gln Lys Asn Trp Leu Arg
    370                 375                 380

His Ser Ile Asp Met Glu Thr Pro Val Leu Glu Asp Ala Leu Glu Arg
385                 390                 395                 400

Leu Lys Ser Phe Cys Asp Arg His Ser Asn Lys Lys Ala Pro Leu Lys
                405                 410                 415

Asp Val Asn Gly Val Lys
            420


<210> SEQ ID NO 17
<211> LENGTH: 1307
<212> TYPE: DNA
<213> ORGANISM: Arabidopsis Thaliana

<400> SEQUENCE: 17

attttgcatc ctaactctat ttatatatct ttgacacaat catttttgct tccgtattct      60

cagtgccgta gcagagtatc taaaccaagg tcttccaaag aagcttaccg cagatgacgt     120

gtttatgact ctgggatgca aacaagctat tgagctcgcg gtagacattc tcgctaaacc     180

gaaagccaac gttttgcttc cgagtcccgg cttcccatgg gacctagtcc gctccatcta     240

caagaacctt gaggtccgcc actataattt ccttccagaa aagaactttg aaatcgactt     300

tgatagcgtc cgagcgctcg tggacgagaa cacatttgcc atatttataa tcaaccccca     360

caaccccaat ggtaacacct actccgaggc tcatctcaaa cagctggctg aactggctaa     420

ggaactcaag attatggtgg tttctgacga ggtttttaga tggacactct ttggtagtaa     480

cccttttgtt cctatgggaa aattctcgtc gatcgtacca gtggttacac tcggatccat     540
```

-continued

```
atcaaaggga tggaaagtcc caggatggcg aactggttgg ctcacgctac atgatctaga    600

cggtgtcttc agaaacacca aggtcttaca agctgctcaa gattttctcc agataaacaa    660

taaccctccg acagttatcc aggcggctat tcctgacatc ttggagaaaa ctcctcaaga    720

gtttttgat aagaggcaga gttttctgaa agataaagta gaatttggtt attctaagct    780

caagtacatt cctagcctca cttgctacat gaaacccgaa gcctgcacct tcttatggac    840

cgagcttgat ttatcgagct ttgtggacat cgaagacgat caagactttt gcaataagct    900

tgctaaagaa gaaaacctcg tcgttttacc agggattgca ttcagtcaga agaactggtt    960

gaggcattct atcgatatgg agactccggt attggaggat gcattggaaa gattgaagag   1020

cttctgcgat cgccattcca acaaaaaagc tcccctcaaa gacgtcaatg gtgttaagta   1080

aagggtcaat atggttattt gcctaagtca tttacgtatg ctataatgat aaataaatga   1140

gtgtttcttg gtttgaggta aatcatgaac actttagtgt atttgtaaca aataaaatgg   1200

gtgcacttaa tatcaatcgt gtgtaatgtt ttctcatagt ttgctatatc tttgtgtata   1260

tctatctact tttcggaaat aaaatagatt gtctgcattt accattg                 1307
```

<210> SEQ ID NO 18
<211> LENGTH: 318
<212> TYPE: PRT
<213> ORGANISM: Arabidopsis Thaliana

<400> SEQUENCE: 18

```
Met Thr Leu Gly Cys Lys Gln Ala Ile Glu Leu Ala Val Asp Ile Leu
1               5                   10                  15

Ala Lys Pro Lys Ala Asn Val Leu Leu Pro Ser Pro Gly Phe Pro Trp
            20                  25                  30

Asp Leu Val Arg Ser Ile Tyr Lys Asn Leu Glu Val Arg His Tyr Asn
        35                  40                  45

Phe Leu Pro Glu Lys Asn Phe Glu Ile Asp Phe Asp Ser Val Arg Ala
    50                  55                  60

Leu Val Asp Glu Asn Thr Phe Ala Ile Phe Ile Ile Asn Pro His Asn
65                  70                  75                  80

Pro Asn Gly Asn Thr Tyr Ser Glu Ala His Leu Lys Gln Leu Ala Glu
                85                  90                  95

Leu Ala Lys Glu Leu Lys Ile Met Val Val Ser Asp Glu Val Phe Arg
            100                 105                 110

Trp Thr Leu Phe Gly Ser Asn Pro Phe Val Pro Met Gly Lys Phe Ser
        115                 120                 125

Ser Ile Val Pro Val Val Thr Leu Gly Ser Ile Ser Lys Gly Trp Lys
    130                 135                 140

Val Pro Gly Trp Arg Thr Gly Trp Leu Thr Leu His Asp Leu Asp Gly
145                 150                 155                 160

Val Phe Arg Asn Thr Lys Val Leu Gln Ala Ala Gln Asp Phe Leu Gln
                165                 170                 175

Ile Asn Asn Asn Pro Pro Thr Val Ile Gln Ala Ala Ile Pro Asp Ile
            180                 185                 190

Leu Glu Lys Thr Pro Gln Glu Phe Phe Asp Lys Arg Gln Ser Phe Leu
        195                 200                 205

Lys Asp Lys Val Glu Phe Gly Tyr Ser Lys Leu Lys Tyr Ile Pro Ser
    210                 215                 220

Leu Thr Cys Tyr Met Lys Pro Glu Ala Cys Thr Phe Leu Trp Thr Glu
225                 230                 235                 240
```

-continued

```
Leu Asp Leu Ser Ser Phe Val Asp Ile Glu Asp Asp Gln Asp Phe Cys
                245                 250                 255

Asn Lys Leu Ala Lys Glu Glu Asn Leu Val Val Leu Pro Gly Ile Ala
            260                 265                 270

Phe Ser Gln Lys Asn Trp Leu Arg His Ser Ile Asp Met Glu Thr Pro
        275                 280                 285

Val Leu Glu Asp Ala Leu Glu Arg Leu Lys Ser Phe Cys Asp Arg His
    290                 295                 300

Ser Asn Lys Lys Ala Pro Leu Lys Asp Val Asn Gly Val Lys
305                 310                 315
```